(12) United States Patent
Wurtman et al.

(10) Patent No.: US 10,092,621 B2
(45) Date of Patent: Oct. 9, 2018

(54) TREATMENT OF ENTERAL FEEDING INTOLERANCE

(71) Applicant: Lyric Pharmaceuticals Inc., South San Francisco, CA (US)

(72) Inventors: David Wurtman, San Francisco, CA (US); Joyce James, Oakland, CA (US); M. Scott Harris, Takoma Park, MD (US)

(73) Assignee: Lyric Pharmaceuticals Inc., South San Francisco, CA (US)

( * ) Notice: Subject to any disclaimer, the term of this patent is extended or adjusted under 35 U.S.C. 154(b) by 0 days.

(21) Appl. No.: 15/526,262

(22) PCT Filed: Nov. 11, 2015

(86) PCT No.: PCT/US2015/060222
§ 371 (c)(1),
(2) Date: May 11, 2017

(87) PCT Pub. No.: WO2016/077498
PCT Pub. Date: May 19, 2016

(65) Prior Publication Data
US 2017/0304395 A1    Oct. 26, 2017

Related U.S. Application Data

(60) Provisional application No. 62/078,888, filed on Nov. 12, 2014.

(51) Int. Cl.
| A61K 38/12 | (2006.01) |
| A61K 9/00 | (2006.01) |
| A61P 1/00 | (2006.01) |
| A61K 38/00 | (2006.01) |
| A61K 31/00 | (2006.01) |

(52) U.S. Cl.
CPC ............ *A61K 38/12* (2013.01); *A61K 9/0019* (2013.01); *A61K 31/00* (2013.01); *A61K 38/00* (2013.01)

(58) Field of Classification Search
CPC ...... A61K 38/00; A61K 9/0019; A61K 31/00; A61K 38/12
See application file for complete search history.

(56) References Cited

U.S. PATENT DOCUMENTS

| 5,756,481 A | 5/1998 | Arnal et al. |
| 7,713,978 B2 | 5/2010 | King et al. |
| 2007/0021331 A1 | 1/2007 | Fraser et al. |
| 2007/0238737 A1 | 10/2007 | King et al. |
| 2009/0259279 A1 | 10/2009 | Dobak, III |
| 2011/0065660 A1 | 3/2011 | Baron et al. |
| 2011/0105389 A1 | 5/2011 | Hoveyda et al. |
| 2011/0245159 A1 | 10/2011 | Hoveyda et al. |
| 2013/0261011 A1 | 10/2013 | Maron et al. |
| 2013/0316002 A1 | 11/2013 | Berner |
| 2015/0099709 A1 | 4/2015 | Takahashi et al. |
| 2015/0265680 A1 | 9/2015 | Matsuo et al. |

FOREIGN PATENT DOCUMENTS

| WO | 2006/009645 A1 | 1/2006 |
| WO | 2006/009674 A1 | 1/2006 |
| WO | 2007/113202 A1 | 10/2007 |
| WO | 2011/041369 A1 | 4/2011 |
| WO | 2016/077498 A1 | 5/2016 |
| WO | 2017/083882 A1 | 5/2017 |
| WO | 2017/097328 A1 | 6/2017 |
| WO | 2017/197131 A1 | 11/2017 |
| WO | 2017/197328 A1 | 11/2017 |

OTHER PUBLICATIONS

PCT/US2015/060222, International Search Report and Written Opinion, dated Jan. 22, 2016, 9 pages.
Ejskjaer et al., Safety and efficacy of ghrelin agonist TZP-101 in relieving symptoms in patients with diabetic gastroparesis: a randomized, placebo-controlled study, Neurogastroenterol Motil., 2010, vol. 22, pp. 1069-1078.
Luttikhold et al., Review article: the role of gastrointestinal hormones in the treatment of delayed gastric emptying in critically ill patients in Alimentary Pharmacology Therapeutics, 2013, vol. 38, pp. 573-583.
Acosta, A. et al. *Relamorelin Relieves Constipation and Accelerates Colonic Transit in a Phase 2, Placebo-Controlled, Randomized Trial*. Clin Gast Hepat, vol. 13, Issue 13. Published Dec. 2015. pp. 2312-2319.
Arabi, Y. et al. *Permissive Underfeeding or Standard Enteral Feeding in Critically Ill Adults*. New England Journal of Medicine, vol. 372. Published Jun. 18, 2015. pp. 2398-2408.
Bochicchio, G. et al. *Ghrelin Agonist TZP-101/Ulimorelin Accelerates Gastrointestinal Recovery Independently of Opioid Use and Surgery Type: Covariate Analysis of Phase 2 Data*. World Journal of Surgery, vol. 36, Issue 1. Published Jan. 2012. pp. 39-45.
Booth, C., et al. *Gastrointestinal Promotility Drugs in the Critical Care Setting: A Systematic Review of the Evidence*. Critical Care Medicine, vol. 30, Issue 7. Published Jul. 2002. pp. 1429-1435.
Camilleri, M. et al. *A Ghrelin Agonist Fails to Show Benefit in Patients with Diabetic Gastroparesis: Let's Not Throw the Baby Out with the Bath Water*. Neurogastroenterology & Motility, vol. 25, Issue 11. Nov. 2013. pp. 859-863.
Chapman, M., et al. *The Effect of Camicinal (GSK962040), A Motilin Agonist, on Gastric Emptying and Glucose Absorption in Feed-Intolerant Critically Ill Patients—A Randomized, Blinded, Placebo-Controlled, Clinical Trial*. Critical Care, vol. 20, Issue 1. p. 232, 2016.

(Continued)

*Primary Examiner* — Julie Ha
*Assistant Examiner* — Li N Komatsu
(74) *Attorney, Agent, or Firm* — Kilpatrick Townsend & Stockton LLP

(57) ABSTRACT

Enteral Feeding Intolerance (EFI) can be efficaciously treated by administration of therapeutically effective doses of ulimorelin every 8 hours (three times a day). Therapeutic benefit can be obtained from single and consecutive daily dosing, including for periods of up to a week or longer.

15 Claims, 7 Drawing Sheets

(56) References Cited

OTHER PUBLICATIONS

Chapman, M., et al. *Gastrointestinal Motility and Prokinetics in the Critically Ill.* Current Opinion in Critical Care, vol. 13, Issue 2. Published Apr. 2007. pp. 187-194.

Deane, A. et al. *Bench-to-Bedside Review: The gut as an endocrine organ in the critically ill.* Critical Care, vol. 14, Issue 5. Published Sep. 2010. p. 228.

Deane, A. et al. *Prokinetic Drugs for Feed Intolerance in Critical Illness: Current and Potential Therapies.* Crit Care Resusc. Published Jun. 2009. 11(2):132-43.

Doherty, W., et al. *Prokinetic Agents in Critical Care.* Critical Care, vol. 7, Issue 3. Published Jan. 2003. pp. 206-208.

Ejskjaer, N. et al. *Ghrelin Receptor Agonist (TZP-101) Accelerates Gastric Emptying in Adults with Diabetes and Symptomatic Gastroparesis.* Alimentary Pharmacology and Therapeutics, vol. 29, Issue 11. Jun. 2009. pp. 1179-1187.

Fazeli, P. et al. *Short-Term Treatment With a Ghrelin Agonist Significantly Improves Gastric Emptying in Anorexia Nervosa.* Endocrine Society's 98th Annual Meeting and Expo. Apr. 1-4, 2016. SUN-606. 2 pages.

Fraser, G. et al. *Effect of the Ghrelin Receptor Agonist TZP-101 on Colonic Transit in a Rat Model of Postoperative Ileus.* European Journal of Pharmacology vol. 604, Issues 1-3. Feb. 2009. pp. 132-137.

Fraser, R., et al. *Current and Future Therapeutic Prokinetic Therapy to Improve Enteral Feed Intolerance in the ICU Patient.* Nutrition in Clinical Practice, vol. 25, No. 1. Published Feb. 2010. pp. 26-31.

Freilich, D. et al. *Imipramine Binding to Alpha-1-Acid Glycoprotein in Normal Subjects and Cardiac Patients.* Clin. Pharmacol. Ther. Published May 1984. 5 pages.

Grant, K., et al. *Prokinetic Drugs in the Intensive Care Unit: Reviewing the Evidence.* Journal of the Intensive Care Society, vol. 10, Issue 1. Published Jan. 2009. pp. 34-37.

Haddley, K. *Relamorelin.* Drugs of the Future, vol. 29, Issue 11. Published Nov. 2014. pp. 775-781.

Hawkyard, C., et al. *The Use of Erythromycin as a Gastrointestinal Prokinetic Agent in Adult Critical Care: Benefits Versus Risks.* Journal of Antimicrobial Chemotherapy, vol. 59, Issue 3. Published Mar. 2007. pp. 347-358.

Huang Z. et al. *Effect of Alpha-1-Acid Glycoprotein Binding on Pharmacokinetics and Pharmacodynamics.* Current Drug Metabolism, vol. 14, No. 2. Feb. 2013. pp. 226-238.

Israili, Z. et al. *Human Alpha-1-Glycoprotein and Its Interactions With Drugs.* Drug Metabolism Reviews, vol. 33, Issue 2. Published Apr. 30, 2001. pp. 161-235.

Lasseter, K. et al. *Ghrelin Agonist (TZP-101): Safety, Pharmacokinetics and Pharmacodynamic Evaluation in Healthy Volunteers: A Phase I, First-in-Human Study.* Journal of Clinical Pharmacolology, vol. 48, Issue 2. Published Feb. 2008. pp. 193-202.

Levinson, B.et al. *Randomized Study of the Efficacy and Safety of SUN11031 (Synthetic Human Ghrelin) in Cachexia Associated with Chronic Obstructive Pulmonary Disease.* e-SPEN Journal. Published Aug. 2012. pp. e171-e175.

Lewis, K., et al. *The Efficacy and Safety of Prokinetic Agents in Critically Ill Patients Receiving Enteral Nutrition: A Systematic Review and Meta-Analysis of Randomized Trials.* Critical Care, vol. 20, Issue 1. Published Aug. 2016. p. 259.

Maclaren, R., et al. *Comparison of Cisapride and Metoclopramide for Facilitating Gastric Emptying and Improving Tolerance to Intragastric Enteral Nutrition in Critically Ill, Mechanically Ventilated Adults.* Clinical Therapeutics, vol. 23, Issue 11. Published Nov. 2001. pp. 1855-1866.

McCallum et al. *Phase 2b, Randomized, Double-Blind 12-Week Studies of TZP-102, a Ghrelin Receptor Agonist for Diabetic Gastroparesis.* Neurogastroenterol Motil, vol. 25, Issue 11. Published Nov. 2013. pp. e705-e717.

Miskovitz, P. *Gastric Prokinetic Motility Therapy to Facilitate Early Enteral Nutrition in the Intensive Care Unit.* Critical Care Medicine, vol. 30, Issue 6. Published Jun. 2002. pp. 1386-1387.

Nagaya, N. et al. *Effects of Ghrelin Administration on Left Ventricular Function, Exercise Capacity, and Muscle Wasting in Patients With Chronic Heart Failure.* Circulation. vol. 110, Issue 24. Published Dec. 2004. pp. 3674-3679.

Palus, S. et al. *Effect of Application Route of the Ghrelin Analog BIM-28131 (RM-131) on Body Weight and Body Composition in a Rat Heart Failure Model.* International Journal of Cardiology, vol. 168, Issue 3. Published Oct. 2013. pp. 2369-2374.

Peeters, T.L. *Central and Peripheral Mechanisms by which Ghrelin Regulates Gut Motility.* Journal of Physiology and Pharmacology, vol. 54, Supplement 4. Published Dec. 2003. pp. 95-103.

Popescu, I. et al. *The Ghrelin Agonist TZP-101 for Management of Postoperative Ileus After Partial Colectomy: A Randomized, Dose-Ranging, Placebo-Controlled Clinical Trial.* Dis Colon Rectum, vol. 53, Issue 2. Published Feb. 2009. pp. 126-134.

Pustovit, R. et al. *The Mechanism of Enhanced Defecation Caused by the Ghrelin Receptor Agonist, Ulimorelin.* Neurogastroenterology & Motility, vol. 26, Issue 2. Published Feb. 2014. pp. 264-271.

Reignier, J., et al. *Erythromycin and Early Enteral Nutrition in Mechanically Ventilated Patients.* Critical Care Medicine, vol. 30, Issue 6. Published Jun. 2002. pp. 1237-1244.

Roberts, D., et al. *Use of Novel Prokinetic Agents to Facilitate Return of Gastrointestinal Motility in Adult Critically Ill Patients.* Current Opinion in Critical Care, vol. 12, Issue 4. Published Aug. 2006. pp. 295-302.

*Tranzyme Pharma and Norgine Announce Top-Line Data From ULISES 008, the Second of Two Phase 3 Pivotal Trials Evaluating Ulimorelin.* Tranzyme Pharma. Published May 25, 2012. 2 Pages.

*Tranzyme Pharma's DIGEST Trial Stopped for Futility After Interim Analysis of the Phase 2b Results.* Tranzyme Pharma. Published Dec. 17, 2012. 1 Page.

Shaw, M. et al. *Safety and Efficacy of Ulimorelin Administered Postoperatively to Accelerate Recovery of Gastrointestinal Motility Following Partial Bowel Resection: Results of Two Randomized, Placebo-Controlled Phase 3 Trials.* Diseases of the Colon & Rectum, vol. 56, Issue 7. Jul. 2013. pp. 888-897.

Ukleja, A. *Altered GI Motility in Critically Ill Patient.* Nutrition in Clinical Practice, vol. 25, Issue 1. Published Feb. 3, 2010. pp. 16-25.

Venkova, K. et al. *Prokinetic Effects of a New Ghrelin Receptor Agonist TZP-101 in a Rat Model of Postoperative Ileus.* Digestive Diseases and Sciences, vol. 52, Issue 9. Sep. 2007. pp. 2241-2248.

Wargin, W. *Contribution of Protein Binding to the Pharmacokinetics of the Ghrelin Receptor Agonist TZP-101 in Healthy Volunteers and Adults with Symptomatic Gastroparesis.* Clinical Drug Investigation, vol. 29, Issue 6. Jun. 2009. pp. 409-418.

Wo, W. et al. *Randomised Clinical Trial: Ghrelin Agonist TZP-101 Relieves Gastroparesis Associated with Severe Nausea and Vomiting—Randomised Clinical Study Subset Data.* Alimentary Pharmacology and Therapeutics, vol. 33, Issue 6. Published Mar. 2011. pp. 679-688.

TREATMENT OF ENTERAL FEEDING INTOLERANCE

CROSS REFERENCE TO RELATED APPLICATIONS

This application is a National Stage Entry of International Application No. PCT/US2015/060222, filed Nov. 11, 2015, which claims the benefit of U.S. Provisional Application No. 62/078,888, filed Nov. 12, 2014.

TECHNICAL FIELD

This application relates generally to formulations, systems, and methods for treatment of Enteral Feeding Intolerance.

BACKGROUND OF THE INVENTION

Enteral Feeding Intolerance (EFI) caused by gastric dysmotility is a serious condition in patients with critical illness admitted to Intensive Care Units (ICU), limiting the ability to administer nutrition. Food is provided to many ICU patients via nasogastric tube or similar device ("enteral feeding"). Malnutrition in the ICU, including protein malnutrition, is associated with poorer long term outcomes including increased mortality (see Malnutrition and Outcomes, Kenneth B. Christopher, M. D., International Symposium on Intensive Care and Emergency Medicine, Brussels, Belgium, Mar. 18-21, 2014). Clinical evidence of improved outcomes associated with the administration of nutrition was established in the ACCEPT study, a randomized controlled prospective trial of 462 evaluable patients that showed that improved ICU nutrition (enabled by protocolized treatment algorithms) resulted in shortened hospital stay (p=0.003) and reduced mortality (trend, p=0.058) (see Multicentre, Cluster-Randomized Clinical Trial Of Algorithms For Critical-Care Enteral And Parenteral Therapy (ACCEPT), Martin et al., CMAJ, Jan. 20, 2004; 170 (2)). Similarly, in a prospective observational cohort study of 113 ICU patients in a tertiary referral hospital, a higher provision of protein and amino acids was associated with lower mortality (Allingstrup et al. 2012 Clinical Nutrition 31 (2012) 462e468).

Gastric dysmotility is problematic in other settings where patients are generally in better health, and a variety of promotility agents have been studied. One of these, ulimorelin (see FIG. 1), has been extensively studied in humans but not yet approved for any human use. Functional activity, as measured by gastric motility and pharmacodynamic (PD) responses, was observed with ulimorelin administered as a 30 min intravenous (IV) infusion once daily in Phase 2 studies in diabetic gastroparesis patients (see Ejskjaer et al., Aliment Pharmacol Ther 29, 1179-1187) and shortened time to first bowel movement (BM) in a Phase 2 study of patients with post-operative ileus following once daily dosing (qD) for up to 7 days (see Dis Colon Rectum 2010; 53: 126-134)). In these Phase 2 studies it was observed that ulimorelin both accelerated gastric emptying of solid and liquid food (10 patients with diabetic gastroparesis) and accelerated recovery of gastrointestinal (GI) function in subjects who underwent partial large bowel resection (168 patients with post-operative ileus). An additional Phase 2 study of diabetic gastroparesis patients showed improvements in GCSI Loss of Appetite and Vomiting scores (see Ejskjaer et al., Neurogastroenterol Motil (2010) 22, 1069-e281). Unfortunately, these initial results failed to generalize as they did not reproduce in two larger prospective randomized, double-blinded, controlled pivotal Phase 3 trials of a postoperative ileus patient population when administered once daily for up to 7 days. In these larger trials, ulimorelin failed to achieve the target clinical endpoint of GI motility in patients who have undergone partial bowel resection.

Critically ill patients with EFI in the ICU are generally more ill than those studied in the ulimorelin Phase 3 trials described above. Given their serious medical condition and a general recognition of the importance of providing enteral feeding to them, these patients are often prescribed a medication in an attempt to restore gastric motility and emptying, even though current medications are unsatisfactory. Current medication choices are limited, as there are no drugs approved by the Food and Drug Administration (FDA) or EMEA, for this clinical indication. Drugs in common usage include metoclopramide and erythromycin, and to a much lesser degree, alvimopan (Entereg®) and methylnaltrexone (Relistor®). While physicians may seek to treat using up to 5-7 day courses and possibly with additional repeated courses with these medications, clinical studies demonstrate that not only is the maximal efficacy of both metoclopramide and erythromycin limited in resolving excessive gastric residual volume (GRV), but also the duration of any such efficacy is short lived, typically shorter than seven days and sometimes as little as one to two days (see Nguyen et al., Crit Care Med 2007 Vol. 35, No. 2). Among other safety concerns, metoclopramide has a "Black Box" warning from the US FDA for CNS toxicity, and use of erythromycin, an antibiotic, for a non-infectious purpose may potentially lead to bacterial resistance to antibiotics. Both of these safety issues are undesirable in the EFI intent-to-treat population.

Accordingly, there remains an unmet and urgent need for new therapies for the treatment of EFI, including in those patients who are critically ill and/or in a specialized care facility such as an ICU. The present invention meets this need and provides methods and pharmaceutical formulations and unit dose forms for the safe and efficacious treatment of EFI in the ICU and other settings.

SUMMARY OF THE INVENTION

In a first aspect, the present invention provides a method for treating EFI, said method comprising administering to a patient in need of treatment thereof a therapeutically effective dose of ulimorelin. In one embodiment, the present invention provides a method for treating EFI in critically ill patients, said method comprising administering to a patient in need of treatment thereof a therapeutically effective dose of ulimorelin. Thus, in accordance with the invention, ulimorelin is indicated for the treatment of enteral feeding intolerance in critically ill patients. In another embodiment, ulimorelin is indicated, in accordance with the invention, for the treatment of gastroparesis and/or delayed gastric emptying in critically ill patients with intolerance to enteral feedings. For treatment of EFI in the ICU, intravenous TID administration of ulimorelin in accordance with the invention provides important therapeutic benefit to these critically ill patients. After EFI is resolved, administration of ulimorelin may be continued for some period of time, optionally with twice a day (BID) or qD administration, to continue to provide therapeutic effect via ulimorelin's anabolic effects when administered as described herein.

Ulimorelin dosed as described herein exerts a number of beneficial anabolic effects, including provision of more calories and/or more protein; increases in growth hormone (GH) including via beneficial spikes in level; and, reduction in inflammation, including via reducing sympathetic tone and/or increasing parasympathetic tone, and dosing may be continued to provide continued therapeutic benefit after resolution of EFI. Accordingly, in one embodiment of the invention, ulimorelin is providing treatment to patients in a catabolic state deemed unhealthy by a treating physician. In this embodiment (EFI has resolved but ulimorelin administration continues qD, BID, or TID), ulimorelin provides anabolic benefit for the treatment of patients.

Patients that benefit, without limitation, include patients in need of anabolic stimulation as a result of lean body mass (LBM) loss, or at potential for LBM loss, due to deprivation of calories and/or protein and/or due to systemic inflammation caused by critical illness such as, for example but without limitation, trauma, sepsis, cardiopulmonary disease, neoplasm, pneumonia and/or other serious infection, surgery, and/or gastrointestinal disease. The anabolic benfit provided by ulimorelin is enjoyed by patients both when being treated for EFI, and after EFI has resolved or enteral feeding has stopped. In one embodiment, the patients are in an unhealthy catabolic state. In another embodiment, the patients are suffering from cachexia or other similar conditions. In any of these embodiments, the increase in growth hormone levels (and corresponding reactions of downstream mediators) and/or decrease in net sympathetic tone resulting from administration of ulimorelin in accordance with the invention can provide beneficial effects on protein turnover or otherwise lead to reduced loss of lean body mass. Accordingly, both for patients with EFI and patients who are receiving the drug for its anabolic effect or both, including critically ill patients and patients recovering from critical illness, the present invention provides important therapeutic benefits, in terms of an increased likelihood of survival, shorter duration of ICU stay, lower total cost for ICU stay or full hospitalization, and/or shorter duration of, or lower total cost of, follow-up care, or some combination of these benefits or others.

In another aspect, the present invention provides methods for providing an anti-catabolic benefit to a patient in the ICU and/or for reversing an ICU patient's elevation of resting energy expenditure, and/or for providing cardioprotective benefit to such an ICU patient. While the invention is not to be bound by any theory or putative mechanism of action, these benefits are believed to arise from ulimorelin's ability to prevent or ameliorate the negative health effects of exaggerated sympathetic tone, just as is accomplished by use of beta blockade in ICU patients today. Accordingly, dosing ulimorelin as described herein at doses in the range of 450 µg/kg TID to 600 µg/kg TID (or higher) can provide a significant anti-catabolic benefit, reverse or at least diminish a patient's elevation of resting energy expenditure, and/or provide cardioprotective benefit to ICU patients or other patients in need of such therapeutic benefit.

Ulimorelin is, in accordance with the invention, an effective drug in patients with EFI, including those who are critically ill, when dosed at therapeutically effective levels that can be obtained via three times daily (TID) dosing. As used herein, TID means three administrations per day. In many embodiments, the three administrations will be given on an eight hour schedule (q8H), i.e., each administration will follow the prior administration by about 8 hours. Generally, each dose will be in the range of 80 µg/kg per administration to no more than about 1200 µg/kg per administration (240 to 3600 µg/kg/day). In many embodiments, each dose will be in the range of 150 µg/kg per administration to no more than about 300 µg/kg per administration (450 µg/kg/day to 900 µg/kg/day). Many patients will benefit, however, from doses in the range of 300 µg/kg per administration to no more than about 1200 µg/kg per administration (900 to 3600 µg/kg/day). For example, some patients will receive additional benefit, relative to doses in the range of 300 µg/kg per administration and lower, by receiving up to no more than about 600 µg/kg per administration (900 to 1800 µg/kg/day). Some patients will receive benefit from doses in the 450 µg/kg to 600 µg/kg TID range. Certain patients, as discussed below, however, may experience additional benefit by even higher doses, e.g. 600 µg/kg per administration (1800 µg/kg/day) to no more than about 1200 µg/kg per administration (3600 µg/kg/day).

When dosing is continued after EFI is resolved to provide anabolic or other nutritional benefit to the patient, dosing may be qD, BID or TID, with each individual dose generally in the same ranges (both per dose and total daily dose) as for TID administration. Typical patients may receive total daily doses, when given BID, of, e.g. 600 µg/kg/day or 1200 µg/kg/day. Typical patients may receive total daily doses, when given qD, including 300 µg/kg or 600 µg/kg.

In various embodiments, daily administration of ulimorelin in accordance with the invention is typically conducted for several consecutive days, often at least for 3, 4, or 5 days or longer, including up to a week or even several weeks. Such embodiments include patients who are being treated only for EFI and patients who get treated for EFI and continue therapy after EFI resolution for continued therapeutic benefit (and this latter class of patients will, on average, have longer ICU stays). Depending on a patient's clinical course, other medical problems, and duration of ICU stay, once approved for use, ulimorelin may be prescribed or used for as little as one or two days, depending on physician judgment and the clinical situation. Those of skill in the art will appreciate that physicians may prescribe ulimorelin treatment as described herein for the entire time a patient is on enteral feeding, once EFI is diagnosed.

As discussed, after EFI is resolved the physician may choose to continue treating for the drug's anabolic effect while the patient is still in the ICU. One reason for this, and there are others, is because resolution of impaired gastric emptying may occur within one or two days. In an alternative, a physician may choose to prescribe ulimorelin for the entire duration of an EFI patient's ICU stay, which, while typically 6-9 days, may be as little as one day or as long as weeks or months. In various embodiments, ulimorelin will be administered for up to 5 or up to 7 days, with the option to provide single or multiple repeat courses of this or a similar duration either sequentially, or with intervening periods off medication, e.g., one to four days off treatment. As but one example, a patient may be prescribed ulimorelin for EFI for a period of time, i.e., 5 to 7 days, but the physician, upon observing the positive therapeutic benefit, may order that the medication be continued until the patient leaves the ICU or is otherwise discharged from the ICU or hospital.

In one embodiment, the invention provides methods for enhancing efficacy and reducing unwanted side effects in some patients in need of treatment for EFI by first measuring alpha 1-acid glycoprotein (AAGP) levels or measuring them concurrent with, or shortly after, initiation of therapy, and adjusting the dose for a given patient based on a determination of what free concentrations of drug will be reached in said patient, given the patient's AAGP levels and the disclosure herein. In these embodiments, a therapeutically effective dose of ulimorelin may be higher than 1200 µg/kg, including doses of up to 2400 µg/kg, for patients with extraordinarily high AAGP levels. In related embodiments, the invention provides methods for determining the dose according to a predetermined value or table of values that provides a dose recommendation for a patient according to a patient's AAGP level. In one embodiment, the physician may be provided a table with two to four values or ranges of values for the AAGP level, with a corresponding drug dose for each range or value.

Significantly, in all the various aspects and embodiments of the invention, and despite the complexity of the pharmacokinetics such as, for example, variable protein binding interactions (in particular with AAGP) required to dose the drug in a therapeutically effective manner, the particular requirement to gain maximal therapeutic benefit by optimizing the speed and degree to which specifically free (unbound) ulimorelin achieves its Cmax (i.e. Cmaxfree), and, the varying conditions that can alter AAGP via incompletely elucidated pathways (and thus the kinetics of reaching Cmaxfree), significant numbers of patients can benefit by receiving a standard dose, e.g. 500 µg/kg TID-600 µg/kg TID (for EFI) or TID/BID/qD (following EFI for anabolic treatment). Furthermore, physicians, in view of the disclosure herein, are provided a path to guide them regarding patients likely to benefit more from higher or lower dosing (whether ab initio or after some short period of treatment at 600 µg/kg or other starting dose).

These and other aspects and embodiments of the invention are described in more detail below.

DETAILED DESCRIPTION OF THE INVENTION

Figure 1:
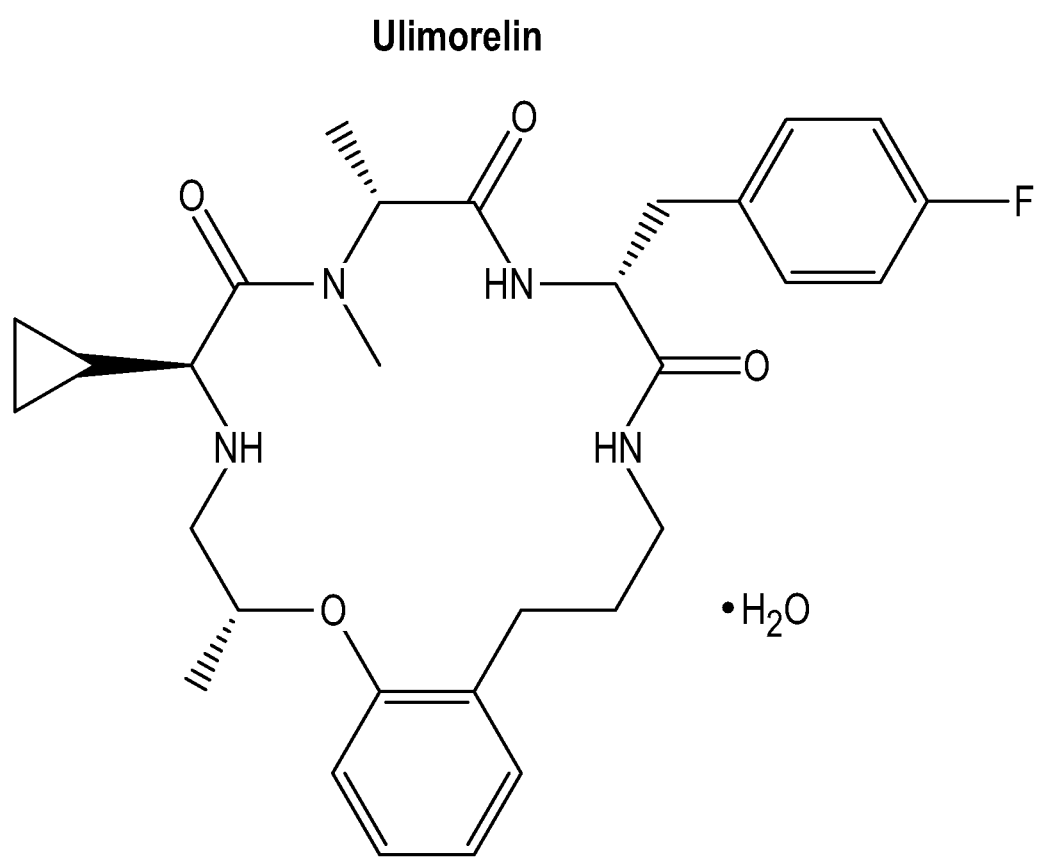
FIG. 1 shows the structure of ulimorelin, also referred to herein as TZP-101, NK42308, or LP101.

Referring now to FIG. 1, ulimorelin (aka TZP-101, LP101, NK42308; see compound 298 in U.S. Pat. No. 8,334,256, incorporated herein by reference), a ghrelin agonist, is a hormone mimetic that is, in accordance with the invention, used for the prevention and treatment of EFI, including EFI recurrences, and prevention and treatment of catabolic effects of critical illness. Enteral feeding is essential for many patients in the ICU setting, and EFI is a condition associated with increased mortality, such that effective treatment can save lives if not at least offer other clinically meaningful patient benefit such as shortened time in the ICU and/or accelerated follow-up recovery or other benefits. As used herein, "ICU" refers to any hospital setting where care is provided to critically or severely ill patients. For example and without limitation, a "burn unit" or any isolation ward (i.e., post-transplant) is an "ICU" for purposes of the invention.

Those of skill in the art will appreciate upon contemplation of this disclosure that ulimorelin, when dosed as described herein (IV administration, TID, at a dose of about 80 µg/kg patient weight to 1200 µg/kg patient weight), in addition to its beneficial effects directly on gastric emptying, exerts a number of beneficial anabolic effects, including provision of more calories and/or more protein; increases in GH including via beneficial spikes in GH level; and/or reduction in inflammation, including via reducing sympathetic tone and/or increasing parasympathetic tone (overall balance referred to herein as "net sympathetic tone"). While the patient with EFI benefits from these activities of ulimorelin dosed as described herein, that same patient, after his or her EFI has resolved, may still receive additional ongoing therapeutic benefit (including preventing recurrence of EFI) from continued administration of the drug as described herein.

Accordingly, the anabolic effects of dosing ulimorelin in accordance with the invention provide additional benefit such that even after enteral feeding is discontinued or EFI is no longer present, administration of ulimorelin as described herein can provide therapeutic benefit to patients in a catabolic state. Such patients may include, without limitation, patients with impaired appetite or impaired food intake; endocrine dysregulation such as, without limitation, impaired GH secretion; inflammatory-mediated catabolism; or, disorders of impaired anabolism, and those of skill in the art will appreciate that such patients include those not previously treated for EFI.

Thus, ulimorelin dosed in accordance with the invention stimulates and restores gastric motility and emptying, and also has anti-catabolic and pro-metabolic (collectively, anabolic) effects. While the invention is not to be limited in terms of putative mechanisms of action, some of these benefits are mediated through hormones such as growth hormone, while other benefits may follow more generally simply from the provision of more protein or nutrition, generally, from administration of ulimorelin as described herein. This treatment can, in effect, both provide more calories and protein to patients in need of such treatment and promote beneficial use of said nutrition to promote augmentation, or decreased loss, of muscle, lean body mass, and/or weight. Treatment with ulimorelin in accordance with the invention can provide beneficial outcomes in patients that include, without limitation, one or more or all of the following, including as compared to patients not treated with ulimorelin: reduction in episodes of excessive GRV (or equivalent) measurements; greater success at provision of a patient's targeted caloric prescription, including without limitation protein requirements; improved beneficial protein turnover; increased lean body mass (LBM); increased ventilator-free days; reductions in frequency of re-intubation episodes, in duration of critical care unit stay, in duration of hospitalization, in hospital-acquired infections, and/or in near term mortality (such as 30- and 60-day); and improvement in various measures of muscle strength and/or functional measures during hospitalization and/or measures of functional status post hospital discharge, including those self-reported by patients and those by their caretakers, such as Activities of Daily Living (ADLs) and Quality Of Life (QOL).

Those of skill in the art will recognize from the foregoing and disclosure and data presented herein that the invention also provides methods for slowing the loss of LBM, for preventing LBM loss, and for increasing LBM. While the benefits of this aspect of the invention begin to accrue early in treatment, significant effects may take one to four weeks to appear; some patients will remain on therapy for much longer, i.e., 90 days or more. Physicians will appreciate that shorter courses of therapy are indicated to prevent or mitigate LBM loss while longer duration treatments should increase or restore LBM, including to the LBM of the patient prior to the injury or disease that placed them at risk of LBM loss. Such patients, include, for example, elderly patients and patients with expected long duration of post-illness/injury recovery and rehabilitation, i.e., patients with hip fractures, as only one of many examples.

The present methods arose in part from the discovery that, to treat EFI in a critical care setting, the promotilty effect (including both acceleration of normal gastric emptying and/or restoration of otherwise impaired or delayed gastric emptying) of a therapeutically active ghrelin agonist will be particularly effective if one achieves maximum plasma concentrations (Cmaxfree) rapidly, followed by a rapid decline. IV administration of the ghrelin agonist ulimorelin in accordance with the invention in normal volunteers (see Example 5) results in Cmaxfree levels in the range of about 0.3 ng/mL (estimated Cmaxfree for an 80 μg/kg dose) to about 125 ng/mL (as measured in a subject receiving a single 1200 μg/kg dose at the end of the 30 minute infusion), with an average effective half-life (T½ alpha) of about 1 hour. Administration of ulimorelin in accordance with the invention provides therapeutically effective blood levels and kinetics.

Achieving a Cmaxfree of about 1 ng/mL should provide meaningful therapeutic benefit in most patients on the first day of administration (in the study reported in Example 5, two healthy volunteers showed 25% and 40% improvement, respectively, in gastric emptying on Day 1 with a Cmaxfree of about 0.5 ng/mL). After consecutive daily administration, ulimorelin Cmaxfree levels generally rise relative to those observed on Day 1. Those of skill in the art will appreciate from the data herein that the present invention provides practitioners a potent and safe drug, because significant therapeutic efficacy is achieved with doses resulting in Cmaxfree of 0.5 to 5 ng/mL, yet a dose that results in Cmaxfree of 125 ng/mL (as measured in the single ascending dose (SAD) study, where the mean for that cohort was 75 ng/mL) was tolerated in the healthy volunteer population. On day one of dosing for patients with normal AAGP levels, a Cmaxfree of 0.5 to 1 ng/mL should provide significant acceleration and/or improvement in gastric emptying. By day 4, higher levels, e.g. 3 to 10 ng/mL, will generally be required to achieve significant acceleration and/or improvement in gastric emptying.

Data analysis of this study indicated that blood levels of 30 ng/mL-125 ng/mL correlated with a reduction in heart rate, and all subjects with a reduced heart rate were asymptomatic. Cmaxfree below about 30 ng/mL also correlated with minor heart rate slowing, but when seen, such slowing was not considered clinically significant and PK/PD modeling predicts heart rate slowing at such Cmaxfree will be less than 10%. Thus, physicians can confidently administer doses resulting in Cmaxfree of at least about 0.5 to 1 ng/mL on Day 1, and 3 to 10 ng/mL on Day 4, in the intent to treat population with certainty that meaningful efficacy to accelerate delayed gastric emptying will be observed and can dose escalate, as needed or desired, up to Cmaxfree levels of 30 ng/mL with confidence that no serious safety issues should arise in the intent to treat population. While higher doses, including those leading to about Cmaxfree values of 75 ng/mL to 125 ng/mL are tolerated, such levels might be avoided in patients with certain types of cardiovascular disease or other conditions where heart rate slowing would be a concern, but should be safe and efficacious in any other patients not receiving adequate therapeutic benefit at a lower dose. The data from the healthy volunteer study described in Example 5, when modeled, demonstrate that patients receiving standard 450 μg/kg TID therapy for EFI with normal AAGP levels should have Cmaxfree values generally in the range of 10-80 ng/mL (predicted mean of about 25 ng/mL). As those of skill will appreciate in view of this disclosure, the 450 μg/kg TID therapy should be safe throughout the EFI population, except potentially those with very low AAGP levels who also cannot tolerate even a minor reduction in heart rate, as discussed below.

Moreover, the standard dose of 500 μg/kg to 600 μg/kg TID should generally be safe and efficacious throughout the EFI population, again, except for patients with very low AAGP levels who also cannot tolerate even a minor reduction in heart rate, and provided that patients with very high AAGP levels may require higher doses, e.g. 750 μg/kg TID or higher, for optimal efficacy, particularly with regard to reducing net sympathetic tone. At doses above 600 μg/kg, it is clear that any mild heart rate slowing and the underlying physiological changes of which such slowing is one manifestation, if seen on consecutive daily administration (in healthy subjects, mild heart rate slowing did not manifest until the SAD of 600 μg/kg), offers important therapeutic benefit for certain patients in the ICU. This mild heart rate slowing, and the underlying physiological changes of which such slowing is one manifestation, can actually provide anti-catabolic benefit to a patient. In one aspect, the present invention provides a method for providing an anti-catabolic benefit to a patient in the ICU. In a related aspect, the present invention provides a method for reversing such a patient's elevation of resting energy expenditure. In yet another related aspect, the present invention provides a method for providing cardioprotective benefit to such a patient. While not wishing to be bound by theory, the inventors believe this aspect of the invention relates to ulimorelin's ability to prevent or ameliorate the negative health effects of exaggerated sympathetic tone.

To reiterate, dosing ulimorelin as described herein at doses in the range of 500 μg/kg TID to 600 μg/kg TID should be efficacious in treating patients with EFI, although dose adjustment may be required for patients with low or very high AAGP levels, relative to normal AAGP levels. Importantly, for some patients, dosing ulimorelin at the high end of the therapeutic range, e.g. 750 μg/kg to 1200 μg/kg TID, can provide a significant anti-catabolic benefit for patients requiring anti-catabolic therapy or otherwise benefitting from a lowering of their resting energy expenditure, particularly if AAGP is elevated. The inventors point to the well-known observation that beta-blocker therapy, such as with propranolol (a nonselective beta-antagonist which also decreases sympathetic tone and shifts the relative physiological balance of parasympathetic vs. sympathetic tone—the "net sympathetic tone"—in favor of parasympathetic tone and also thereby results in mild heart rate slowing) has been associated with improved nutritional status. It will be obvious to those skilled in the art that excess net sympathetic tone in the intent to treat population may lead to unhealthy catabolism and hypermetabolism. Indeed, in children with burns, for example, treatment with propranolol has been used to attenuate hypermetabolism and reverse muscle-protein catabolism, and these patients should benefit from the therapies of the invention as well. Furthermore, in an open-label, randomized Phase 2 study of intensive care unit patients with severe septic shock receiving the short-acting beta-blocker esmolol, the twenty-eight day mortality of 49.4% in the esmolol group vs 80.5% in the control group demonstrated that this therapeutic approach has significant promise. In accordance with the invention, ulimorelin can be dosed at doses of, e.g., 600 µg/kg to 1200 µg/kg TID or higher, particularly doses in the 750 µg/kg to 1200 µg/kg TID range to achieve this benefit (after EFI is resolved qD or BID administration may also be used).

While the invention is not to be limited by theory of mechanism of action, and while, at present, physicians have no experience in using it to treat EFI, the present inventors believe that, upon approval and widespread use, two general types of treatment regimen may be widely practiced. For patients with EFI and also other relevant conditions and/or complications where bradycardia may be an issue or concern, EFI will be treated at efficacious doses unlikely to cause even mild slowing of heart rate (e.g. 150 µg/kg to 300 µg/kg TID or, and particularly if AAGP is elevated, even to 600 µg/kg), where some reduction of net sympathetic tone may occur yet no, or only mild, slowing of heart rate. When AAGP levels are low or normal, which, of course, is uncommon in the ICU population, doses will typically be used in the lower part of this range. However, for patients where there are no such concerns and/or the mild slowing of heart rate provided by ulimorelin as dosed herein is desirable both for itself and also as a signal that a reduction in net sympathetic tone has been achieved, for the reasons described above, physicians may give 600 µg/kg TID or higher doses up to about 1200 µg/kg TID, e.g. 750 µg/kg to 1200 µg/kg TID. Patients receiving 750 µg/kg TID or higher doses should benefit significantly from the reduction in net sympathetic tone, i.e., the shifting of the relative balance of sympathetic to parasympathetic tone in favor of more parasympathetic, including, for example and without limitation, patients with conditions of high sympathetic stress such as septic shock, provided, however, that patients with exceptionally high AAGP levels may not be able to achieve this benefit (net reduction in sympathetic tone).

For treating EFI in accordance with the invention, one desires to achieve the target Cmaxfree rapidly, and for this purpose, IV administration is used. Ghrelin is one of two GI hormones (the other being motilin) that are released in a fasting state to stimulate GI motility via the migrating motor complex (MMC) and related mechanisms. Ghrelin IV injection accelerates gastric emptying of a meal in humans (Binn et al., 2006, Peptides, 27(7): 1603-1606). The IV administration of the methods of the invention have advantages as compared to an oral therapy, in that, in impaired gastric emptying in the critical care setting, GI absorption of an oral drug will be impaired by the same underlying motility problem as one is attempting to treat.

As compared to a subcutaneous therapy, IV administration avoids the pharmacokinetic limitations of a subcutaneous route. In particular, subcutaneous absorption may be unreliable in ICU EFI patients, due, among other factors, to commonly impaired perfusion of subcutaneous tissue due, for example, to hemodynamic instability such as shunting, local or systemic hypotension or circulatory collapse (Fries, 2011, Wien Med Wochenschr 161/3-4: 68-72). In addition to the drawbacks noted above, oral administration is even less desirable, given the widely variable absorption kinetics and thus blood level kinetics in the intent to treat population. IV administration results, through pharmacotherapy, in an effect on gastric and upper GI musculature, including via MMCs, that is as nearly simultaneous to that which occurs in natural human pharmacology as can be achieved with a drug. Similar pharmacokinetics might possibly be achieved via inhalational administration, but this is not practical for the intent to treat population (many of whom are on mechanical ventilation) even if such formulations were available. Hence, for the administration of ulimorelin to restore gastric emptying in a critically ill patient with EFI, the IV route of the present invention provides distinct advantages over other routes of administration.

In accordance with the methods of the invention, ulimorelin can be administered as a 30 minute intravenous (IV) infusion three times daily (TID), typically at approximately 8 hour intervals (q8H). Such a frequency of dosing, particularly when accomplished with IV administration, best mimics the natural state of thrice-daily (i.e. meal-related) ghrelin surges in humans, whether a critically ill patient is being fed by bolus, continuous drip, or a combination of each. The stomach can hold generally about 1 liter of food (see Sherwood, Lauralee (1997)). Human Physiology: From Cells to Systems. Belmont, Calif.: Wadsworth Pub. Co]. Typical enteral feeding in the ICU is given at maximal infusion rates of 80 to 100 mL/hour, or 640 to 800 mL over eight hours. In instances where feeding is given by bolus, typical boluses will not exceed 250 mL. Thus, a q8H or TID dosing regimen will provide gastric emptying events and frequency thereof sufficient to ensure for most patients that the volume of food given between doses will not exceed the innate capacity of the stomach; more frequent dosing would add cost and complexity to the patient's care and add potential risk, but without expected additional benefit.

Typically, each dose is in the range of 80 µg/kg to 1200 µg/kg, with various substantial patient groups receiving benefit from administering ulimorelin in doses of 150 µg/kg to 300 µg/kg and 300 µg/kg to 600 µg/kg. Generally, patients with AAGP levels in the "normal" range and higher will receive doses in the range of 300 µg/kg to 1200 µg/kg, with many patients receiving 500 µg/kg TID to 600 µg/kg TID. However, doses of 300 µg/kg TID, or any dose between 300 µg/kg TID and 600 µg/kg TID, will be efficacious in many patients even if most receive a dose in the standard 500 µg/kg-600 µg/kg TID range. For example, most patients may receive 600 µg/kg TID, or higher if they have AAGP levels that are exceptionally high. For patients with below normal AAGP levels, the treating physician may elect to administer doses in the 80 µg/kg to 300 µg/kg range, with many patients receiving 300 µg/kg TID. For patients whose illness or disease materially changes drug metabolism/excretion (clearance), physicians may choose instead to administer doses and measure Cmaxfree, as described above, to ensure that the dose administered is safe and achieves the Cmaxfree required for efficacy.

For some patients, ulimorelin will be administered as a 30 min intravenous (IV) infusion q8H (TID) at 80 µg/kg, 150 µg/kg, 300 µg/kg, 450 µg/kg, 500 µg/kg, 600 µg/kg, 750 µg/kg, 900 µg/kg, or 1200 µg/kg. For other patients, ulimorelin will be dosed as a 30 min infusion q8H or TID at doses higher than 1200 µg/kg, as determined based on individual AAGP levels significantly exceeding a predetermined "normal" level. Infusion times and practices may vary in accordance with physician practice; the guidance here enables the ordinarily skilled artisan to employ any conventional infusion practice, including, without limitation, use of IV bags or use of syringe pumps. Other patients will benefit, as discussed above, by receiving these same doses (or total daily amounts) administered BID or qD, i.e., patients not on or no longer needing enteral feeding or no longer intolerant to enteral feeding but still in a catabolic or other state where the treating physician believes the anabolic effects of dosing ulimorelin in accordance with the invention will provide therapeutic benefit.

Treatment of EFI in a critical care setting in accordance with the methods of the invention will be particularly beneficial in that ulimorelin, when administered as a promotility drug in accordance with the invention, has additional benefits to patients. Ulimorelin counteracts the occurrence of a catabolic state in such patients, one that many such patients may experience. In a situation wherein adequate nutrition is not provided, such patients can lose as much as 1 kilogram of lean body mass per day. Even when food is provided, due to the heightened state of illness and the attendant effort of the body to repair and heal, as well as a frequent state of inflammation that also drives a hyper-catabolic state and/or excessive net sympathetic tone, loss of lean body mass may occur and can be significant and debilitating, both in the short and long term.

Ulimorelin is a therapeutic agent with both anti-catabolic and anti-inflammatory properties, that also restores gastric emptying, and so it is particularly efficacious for the treatment of EFI, including treatment in the ICU setting, and for providing anabolic benefit and/or reducing excessive net sympathetic tone, whether in the ICU setting (during and post-EFI) or elsewhere. Thus, in one embodiment of the invention, ulimorelin is administered to a patient in a hyper-catabolic state (a catabolic state that a physician deems unhealthy) and can provide enhanced therapeutic benefit as compared to other agents, such as motilin agonists and 5HT-4 agonists, although such agents may be used in combination with ulimorelin in accordance with the invention to provide additional therapeutic benefit. Typically these other agents will offer a promotility benefit only.

Thus, in one important embodiment of the invention, ulimorelin is administered to treat EFI. Example 5, below, describes a study in healthy volunteers that showed administration of ulimorelin as described herein substantially improved liquid gastric emptying as compared to placebo over baseline measurements (see discussion below). Those skilled in the art will appreciate that, for healthy volunteers who have normal gastric emptying at baseline, "improvement" is measured as acceleration of gastric emptying rate (measured in units of time) above baseline physiologic levels, and this translates in the intent to treat population—patients with impaired and/or delayed gastric emptying—as restoration of gastric emptying times to those, or closer to those, of the patient's pre-morbid condition. The notable acceleration in upper GI motility (a prokinetic effect of ulimorelin when used in accordance with the invention) seen in healthy volunteers is consistent with the discovery that achievement of optimized Cmaxfree kinetics and levels are each a key requirement for successfully using ulimorelin to treat EFI.

In the methods of the invention, one desires to achieve a Cmaxfree of at least about 0.5 ng/mL to 1 ng/mL but typically not exceeding about 125 ng/mL, which is critical for therapeutic efficacy without undue risk of serious side effects in patients whom may be harmed by excessive reduction in heart rate. Thus, in one embodiment, the present invention provides methods for improving (accelerating) gastric emptying in patients in need of such treatment, such methods involving administration of ulimorelin as described herein, and such methods typically resulting in a Cmaxfree after each administration in the range of 1 to 30 ng/mL, depending upon when in the course of therapy Cmaxfree is measured. These methods are suitable for use in treating patients with EFI and other indications where the prokinetic effects of ulimorelin are therapeutically beneficial in the amounts and with the treatment regimens described herein.

In another aspect of the invention, ulimorelin is administered to a patient in a catabolic state (which itself may be due to or exacerbated by an underlying inflammatory condition) that is deemed harmful by the treating physician. Ulimorelin can be used in accordance with the invention to improve provision of calories, to improve gastric motility, to promote maintenance or lessened loss of lean body mass, to reduce an underlying inflammatory state contributing to a catabolic state such as systemic inflammation caused by critical illness including, for example but without limitation, trauma, sepsis, cardiopulmonary disease, neoplasm, pneumonia and other serious infection, surgery and/or gastrointestinal disease, to treat a catabolic state directly, and to promote beneficial outcomes such as may result from improved maintenance of lean body mass. As compared with ICU EFI (and other) patients who either receive no therapy or a different therapy that does not offer these benefits, patients receiving ulimorelin should generally have greater likelihood of surviving their ICU stay or other illness and, for those who do survive, of requiring enteral feeding and/or critical care for shorter period of time. Such patients may include, without limitation, patients with impaired appetite or impaired food intake; endocrine dysregulation such as, without limitation, impaired GH secretion; inflammatory-mediated catabolism; or, disorders of impaired anabolism, and those of skill in the art will appreciate that such patients include those not previously treated for EFI. While not wishing to be bound by any theory of the invention, these benefits are believed to arise, at least in part, from the increase in GH levels attendant to administration of ulimorelin in accordance with the methods of the invention.

Administration of ulimorelin in accordance with the present invention results in GH level "spikes", and in healthy volunteers receiving 150 µg/kg TID, GH levels spiked to ~11 µg/L and ~19 µg/L in males and females, respectively, on Day 1, and while levels declined over time (see Example 5), the spikes seen after repeat administration remained clinically significant. Thus, the methods of the invention can provide therapeutically meaningful anti-catabolic (anabolic) effect without undue risk of serious side effects. Thus, in one embodiment, the present invention provides methods for increasing GH levels in patients in need of such treatment, such methods involving administration of ulimorelin as described herein, and such methods resulting in GH spikes after each administration of at least about 2 µg/L (male) and about 6 µg/L (female). In some embodiments, the patients' GH levels are returned to near normal levels (0 to 0.8 µg/L in males, and 0 to 8 µg/L in females). These methods are suitable for use for providing an anabolic effect in patients in need of treatment, including patients in a catabolic state deemed harmful by the treating physician and in patients with cachexia. In these methods, ulimorelin is administered in the amounts and with the treatment regimens described herein (typically TID if patient also suffering from EFI; qD, BID, or TID if not).

In various embodiments of both of these aspects of the invention, the invention relates to the use of an ulimorelin drug product concentrate provided for use in the invention that is packaged in glass vials, a unit dose form of the invention, as 2 mg/mL filled with approximately 10.5 mL/vial, typically between 10-11 mL per vial, in buffered 5% dextrose in water for injection and labeled for use in accordance with the invention. The invention provides many other useful embodiments of ulimorelin formulations suitable for IV administration and drug products containing such formulations.

Thus, ulimorelin drug product concentrate provided by the invention includes larger volume unit dose forms (vials) and packaging providing higher fill volumes at, for example, 20 mL, 25 mL, 50 mL, and 100 mL per vial volume and corresponding fill amounts, or values in between these amounts; the invention also provides drug product, in approximately 10 mL per vial volume packaging with formulations at higher concentrations, such as 3 mg/mL, 4 mg/mL, 5 mg/mL, or 6 mg/mL; and provides products with both higher concentration formulations, such as 3 mg/mL, 4 mg/mL, 5 mg/mL, or 6 mg/mL, and in larger volume packaging and correspondingly higher fill amounts at, for example, approximately 20 mL, 25 mL, 50 mL, and 100 mL per vial or values in between these amounts. These concentrations refer to the TZP-101 for Injection formulation of the drug (see below) and similarly soluble salts. In accordance with the invention, formulations of other ulimorelin salts are provided that may be used when more concentrated drug solutions are desired. Alternate, higher solubility, therapeutically effective ulimorelin salts suitable for use in these embodiments of the invention include, without limitation, the succinate and malate salts, and the invention provides drug products for such salts and the formulations containing them.

In one embodiment, the ulimorelin used in a method of the invention is provided as TZP-101 for injection, labeled as LP101. This formulation was used to obtain the results reported in Example 5, below. The TZP-101 formulation is at 2 mg/mL in the vial. While it can be administered "neat", it is often (as was the case in the study in Example 5) diluted before use. More concentrated formulations, can be used to prepare other drug products of the invention. TZP-101 for Injection is a sterile, pyrogen-free solution of ulimorelin hydrochloride monohydrate (equivalent to 2 mg/mL of ulimorelin free base) in water for Injection buffered to pH 4.5 with 10 mM acetate buffer, and containing dextrose for tonicity adjustment. Other drug product presentations of the invention can be prepared with these or alternate excipients, as discussed further below.

Those of skill in the art will appreciate that the invention may be practiced with various enantiomeric mixtures containing TZP-101 or close structural analogs (and enantiomerically pure and mixtures) of similar biological activity without deviating from the scope or spirit of the invention. Suitable such mixtures and close structural analogs are disclosed in, for example and without limitation, U.S. Pat. Nos. 7,452,862; 7,521,420; 8,129,561; 8,334,256; and 8,440,851; U.S. Patent App. Pub. No. 20080194672; and PCT Pub. Nos. 2005/012331; 2006/009645; and 2006/009674, each of which is incorporated herein by reference.

For the TZP-101 for Injection formulation, the drug product presentation (or "drug product intermediate" in some situations) is a clear vial filled with 10 mL (10.5 mL) of solution closed with rubber stoppers and flip-off aluminum seals. The product is intended to be diluted, as needed, to the desired concentration and administered by IV infusion over 30 minute using a syringe pump (other devices may be readily substituted in view of the disclosure herein based on the ordinarily skilled physician's personal practices and patient needs). The pharmacokinetics achieved via a 30 minute infusion time provides the desired Cmaxfree at the desired kinetics to provide therapeutic benefit to EFI patients. Those skilled in the art will appreciate that when guided to a 30 minute infusion time, actual delivery time for drug given by a healthcare provider may vary, typically by no more than +/−5 minutes.

Suitable infusion concentrations may be, for example, in the range of 0.15 mg/mL to 1.00 mg/mL. In alternate embodiments, suitable infusion concentrations may be in the range of 1.00 mg/mL-2.00 mg/mL. Infusion temperature is typically room temperature (infusion bags may be stored refrigerated or at room temperature, and the LP101 is typically stored at controlled room temperature), and the infused product typically has a pH of about 4.5 (the approximate pH of the infusate used in Example 5). The cannula for infusion may be 22 gauge or larger (for adults). Phlebitis, should it occur with a given infusion, can be prevented by good clinical practice or by infusion through a central line.

In a typical application of the methods and products of the invention, the body weight of a patient in need of treatment for EFI is measured or estimated to calculate the actual dose for each administration of drug. For the doses reported herein, it is assumed that the physician will use total body weight. However, some physicians may use "ideal body weight" dosing if a patient is particularly obese, or may make other adjustments not indexed to body weight such as sometimes is done in clinical practice for particularly obese patients. Similarly, some physicians may use "ideal body weight" if a patient is particularly emaciated. In yet further embodiments, some physicians, when guided by their clinical judgment, may dose according to pre-morbid body weight ("usual body weight"), such as, by way of non-limiting example, to account for the effect of overhydration on measured body weight such as can occur during resuscitation of a patient with unstable cardiovascular status. In cases such as these, pre-morbid body weight will typically be lower than measured body weight. Absent other circumstances as discussed herein (e.g. variations in AAGP levels, etc.), however, the doses provided herein are generally suitable regardless of which weight metric is used, as the dose can be increased if insufficient efficacy is seen due to, for example, the physician using ideal body weight dosing for a particularly obese patient or using pre-morbid dosing, e.g., for a fluid-overloaded patient, and, similarly, a dose can be adjusted downward if the physician suspects blood levels may be too high, e.g., after using ideal body weight dosing in an emaciated patient.

Once the dose is determined, the formulation for administration is prepared. For example, to achieve a 600 µg/kg dose in a 70 kg patient requiring treatment for EFI, 21 mL of ulimorelin drug product concentrate (as described above at 2 mg/mL) can be diluted into 100 mL 5% dextrose in water (D5W), which is then administered as constant rate infusion over 30 minutes. Likewise, for 300 µg/kg, 500 µg/kg, 900 µg/kg, 1200 µg/kg, or 2400 µg/kg dose levels, 10.5 mL, 17.5 mL, 31.5 mL, 42 mL, or 84 mL of ulimorelin drug product concentrate is diluted, typically into 50 mL but optionally up to about 100 mL D5W which is then administered at a constant rate infusion over 30 minutes. Those skilled in the art will appreciate that the choice of 50 mL or 100 mL or, indeed, another volume of total infusate (including lower volumes, e.g. as low as 10 to 15 mL, some of which low volumes may be for doses that are given "neat"), may be determined by other factors, including, without limitation, a patient's more general fluid requirements or restriction, and the physician may use appropriate clinical judgment to decide the preferred total volume. This is repeated roughly every 8 hours (q8H) for intervals of up to 5-7 day or longer until feeding goals are achieved or as clinically indicated. Of course, here, too, individual physician (including any other medical professional operating under the physician's direction) practice can vary widely without departing from the scope of the invention. As but illustrative examples, the physician may chose to use a different volume, e.g., 50 mL vs 100 mL or any other amount; to use no diluent (i.e., to use a "neat" administration); or to use a different diluent such as Lactated Ringer's or Normal Saline.

Some patients will benefit from dosing adjusted according to the patient's levels of alpha 1-acid glycoprotein (AAGP; aka orosomucoid), and the present invention provides methods and products useful in treating such patients. In healthy subjects, AAGP ranges from about 550 to 1400 μg/mL have been reported (see Israili and Dayton, *Drug Metabolism Reviews,* 33(2), 161-235 (2001); Kremer et al., *Pharmacol. Rev.* 1988, 40, 1-47; Lentner, C. Documenta Geigy Scientific Tables, *Physical Chemistry, Blood, Somatometric Data,* 8th Ed., Ciba Geigy Corporation: West Caldwell, N.J., 1984: Vol. 3, 135-137, 140-142; Schmeling et al., *Exp. Clin. Immunogenet,* 1986, 13, 78-83.159; Lyngbye and Kroll, *Clin. Chem.* 1971, 17, 495-500.160; Blain et al., *Br. J. Clin. Pharmacol.* 1985, 20, 500-502.161; and Israili et al., [abstract]. Fed. Proc. 1985, 44, 1124).

However, AAGP is an acute phase reactant protein, and levels can be considerably altered in patients, including those who are critically ill. Positive acute phase response proteins are reportedly upregulated during the response and increased levels in the plasma become measurable within hours following a single inflammatory stimulus (see Israili and Dayton, supra; Gruys et al., J Zhejiang Univ SCI 2005 6B (11):1045-1056). After a single stimulus, the levels of these proteins reportedly remain elevated for at least 24 hours and typically decrease starting after about 48 hours, although if the medical condition(s) leading to the upregulation persists, then AAGP levels may remain elevated for longer, generally until resolution of the condition(s) [Gruys et al., supra].

Plasma levels of AAGP reportedly increase in various disease states (acute illness, infection, various types of cancer, cardiovascular disease, central nervous system disorders, diseases of the kidney, liver, and lung, chronic inflammatory diseases, and the like) (see Boucher et al., *Crit Care Clin* 22 (2006) 255-271; Taguchi et al., Chapter 6: Molecular Aspects of Human Alpha-1 Acid Glycoprotein—Structure and Function, from Acute Phase Proteins, edited by Sabina Janciauskiene, InTech, 2013; Israili and Dayton, supra; and Gruys et al., supra). AAGP levels are reportedly higher in obese individuals and in patients with injury, trauma, and severe burns and in recipients of bone marrow and organ transplants (see Israili and Dayton, supra; Eap et al., Clin. Pharmacol. Ther. 1990; 47, 338-346; Benedek et al., Br. J. Clin. Pharmacol. 1984, 18, 941-946; Bloedow et al., J. Clin. Pharmacol. 1986, 26, 147-151; Macfie et al., 1992, 69, 447-450; Wilkinson, Drug Metab. Rev. 1983, 14, 427-465; Raynes, 1982, 36, 77-86; Booker et al., Br. J. Anaesth. 1996, 76, 365-368; and Comments in Br. J. Anaesth. 1996, 77, 130). Elderly patients with acute illness or with cachexia of chronic disease also reportedly have elevated AAGP levels (Israili and Dayton, supra; Lyngbye and Kroll, Clin. Chem. 1971, 17, 495 500; and Verbeeck et al., Eur. J. Clin. Pharmacol. 1984, 27, 91-97). The levels of AAGP reportedly rise after surgery, peaking at 3 to 4 days postoperatively, and then decline to baseline values after 2 to 4 weeks (Israili and Dayton, supra; Hanada et al., Int J Clin Pharmacol Ther 2011; 49(7):415-421; Comments in Br. J. Anaesth. 1996, 77, 130; Garfinkel et al., Ann. Intern. Med. 1987, 107, 48-50; and Jungbluth et al., J. Pharm. Sci. 1989, 78, 807-811).

In some patients, the acute-phase response is reportedly either incomplete or absent. Lower than normal levels of AAGP in plasma have reportedly been found in patients with pancreatic cancer, hepatic cirrhosis, hepatitis, hyperthyroidism, and malnutrition (Israili and Dayton, supra; Trautner et al., Scand. J. Urol. Nephrol. 1980, 14, 143-149; Pacifici et al., Ther. Drug. Monit. 1986, 8, 259-263; and O'Connor and Feely, Clin. Pharmacokinet. 1987, 13, 345-364).

The present inventors were the first to appreciate that, to achieve therapeutically efficacious dosing of ulimorelin, the key PK parameter was not Cmax for the total drug, but the Cmax of the free, unbound form (Cmaxfree), which has a markedly shorter half-life (effective half-life, T½ alpha, of about one hour). Accordingly, not only must ulimorelin be dosed so as to achieve Cmaxfree rapidly, but also, as discussed above, the Cmaxfree should generally be in the range of 0.5 to 125 ng/mL. As described herein, however, there may be two general classes of patients: those being treated primarily for EFI and those being treated for EFI whose physicians believe reduction in net sympathetic tone to be therapeutically important. For the former group, typically receiving 300 μg/kg to 600 μg/kg TID, the mean Cmaxfree (at steady state) is expected to be in the range of about 10 to 45 ng/mL, for patients with normal AAGP levels (if AAGP levels are 2× normal, then Cmaxfree at this dose range would be expected to be in the range of 5-25 ng/mL). For the latter group, typically receiving 750 μg/kg TID to 1200 μg/kg, the mean Cmaxfree will typically be much higher, including some individual patients, receiving doses at the high end of the range, whose Cmaxfree may exceed 125 ng/mL.

An increase in AAGP levels in patients may reduce efficacy by decreasing the free plasma concentrations of ulimorelin. A decrease in AAGP levels may reduce safe dosing margins and potentially cause toxicity by increasing the free plasma concentration of ulimorelin. In accordance with the invention, while it is important to achieve a Cmaxfree quickly after administration, it is also important not to exceed levels where the risk of toxicity outweighs any potential benefit of giving such a high dose. While doses up to 1200 μg/kg (single) have been administered to normal healthy volunteers and were safe and well tolerated, a dose-related reduction in heart rate was observed starting at a Cmaxfree of about 30 ng/mL, and while this slowing did not meet the criteria for an adverse event in the study in which it was observed, subjects receiving the 600 μg/kg, 900 μg/kg, and 1200 μg/kg doses in the SAD study exhibited increased slowing (see Example 5), indicating that bradycardia could occur at higher doses.

Those of skill in the art will recognize that, while bradycardia may be a clinically meaningful finding warranting safety concerns in a subset of the intent to treat population, the etiology is likely due to exaggerated pharmacology of vagally-mediated (i.e. parasympathetic) tone or conversely decreased sympathetic tone. This heart rate slowing is predictable, observable, treatable, and reversible, either with drug withdrawal or passage of time or other means (e.g. atropine), it is unlikely to be a detriment in clinical practice. Furthermore, as noted above, the mild slowing observed in healthy volunteer signifying decreased net sympathetic tone can translate into an important anti-catabolic effect and/or reduction of resting energy levels that may be desirable for many ICU patients and may also act to improve cardiac function. Nonetheless, a dose that may be beneficial for one patient may not be the optimal dose for another. For some patients, a dose which may have been safely and efficaciously administered on a given day may no longer be safely or efficaciously administered on a different day, and this is of particular concern with ulimorelin, given the potential for an intercurrent increase or decrease in the patient's AAGP levels during a course of therapy in the ICU.

Considering the known potential for altered AAGP levels in ill and injured patients, measuring the range of AAGP in the expected ICU (or other intent to treat) population that will receive treatment with ulimorelin will aid in the understanding of the proportion and/or subset(s) of patients that will have AAGP levels higher (or lower) than the normal range and, therefore, could benefit from AAGP adjusted dosing, relative to the dose a patient would receive if AAGP levels were lower (or higher) in that patient. Those of skill in the art will appreciate that, while this aspect and these embodiments of the invention have been discussed with reference to treating EFI in the ICU, they are equally applicable to patients in need of treatment for EFI but not in the ICU as well as those patients, even if not suffering from EFI, who are taking ulimorelin in accordance with the methods of the invention for its anabolic effect.

Undertaking their own studies, the inventors discovered that their findings were markedly different from the AAGP levels reported in the literature. For example, the Randox assay cites "normal" levels of 50-120 mg/dL, but of the healthy volunteer population tested using that assay (as described in Example 5), approximately 70% of the subjects had values between 40-60 (range of ~30 to ~80 mg/dL), leading the inventors to question whether a value as high as 120 is normal. Excitingly, however, while the complexities of AAGP-based dosing may be important for some small subset of patients, the results demonstrated herein demonstrate that significant therapeutic benefit can be provided to large numbers of patients with standard doses in the 150 µg/kg to 600 µg/kg range, with most patients benefiting from doses in the 300 µg/kg to 600 µg/kg range (TID for EFI or qD, BID, or TID for anabolic effect post EFI), with doses of 500 µg/kg TID to 600 µg/kg TID, including, e.g. a standard 600 µg/kg dose TID, being preferred for EFI.

The present invention arises, in part, from the discovery that efficacious gastric emptying with ulimorelin requires adequate maximal free concentrations, Cmaxfree (of at least 0.5-1 ng/mL; see Example 5 below) of the drug and that drug bound to AAGP is not available to interact with the receptor target. Moreover, any free drug (released off AAGP) is rapidly cleared. Furthermore, the inventors recognized that given the wide but poorly characterized variability of AAGP in the intent to treat population, there would be a further challenge to achieving Cmaxfree in a useful number of patients with standard dosing. The present inventors were the first to calculate the half-life of free drug (unbound to AAGP) and show it to be significantly shorter than that of total serum drug; this calculation demonstrates that the TID dosing required by their method should be optimal for EFI patients, as it will provide sufficient promotility effects throughout the day if the proper dose is administered, as provided herein. More importantly, with new understanding of the variability of AAGP levels in the intent to treat population and its implications, and a new understanding of the unexpectedly broad range of therapeutically efficacious and safe Cmaxfree, the inventors subsequent efforts demonstrate that most EFI patients should be treatable with standard dosing (500 µg/kg TID to 600 µg/kg TID) as described herein.

Nonetheless, while many patients can be treated efficaciously by treatment with ulimorelin in accordance with the invention (e.g., q8H—TID—IV administration of 80-1200 µg/kg ulimorelin, e.g. 300 µg/kg to 600 µg/kg TID) without requiring any measurement of AAGP levels, some patients with altered AAGP levels may benefit from adjusting the dose based on the measured AAGP level to ensure the drug is safely and/or efficaciously administered to that patient. This method can result in improved therapeutic efficacy and reduce the likelihood of an adverse event. Levels of AAGP, also known as orosomucoid, are routinely measured by physicians for other purposes (as a prognostic or management factor for certain disorders, such as inflammatory bowel disease; see Kjeldsen et al., Scan. J. Gastroenterol. 1997, 32, 933-941; Gupta et al., Journal of Medical Microbiology (2010), 59, 400-407).

In accordance with this invention, AAGP levels, if measured during a course of treatment with ulimorelin as described herein, can be measured at any time, i.e., immediately before the first administration of ulimorelin, concurrent with initial administration, or after the first (or any subsequent) administration (i.e., testing is "during administration" or concurrent with administration). Assays to determine AAGP or orosomucoid levels suitable for use in accordance with the present invention are readily available commercially at facilities that routinely analyze clinical samples using technologies such as ELISA or nephelometry (see Genway Biotech, Human Orosomucoid (Alpha-1-Acid Glycoprotein) ELISA Quantitation Kit (see world wide web at genwaybio.com; Randox, Alpha-1-Acid Glycoprotein (AGT) RX Series (see world wide web at randox.com)).

Thus, the dose of ulimorelin can be adjusted in accordance with the invention based on measured AAGP levels to achieve a target free plasma concentration ($C_{pfree}$) of ulimorelin (see Freilich and Giardina, Clinical Pharmacology and Therapeutics (1984) 35, 670-674, incorporated herein by reference, for an example of such a calculation; see also, Example 3). As ulimorelin concentrations increase, free fraction increases and the ratio of ulimorelin/AAGP that results in a given free fraction can be determined. Therefore, this ratio can be maintained, in accordance with the invention, by adjusting the dose in patients with lower or higher AAGP levels, as required or helpful.

The target $C_{pfree}$ (Cmaxfree) can be maintained in patients by measuring the AAGP levels daily (but rarely more than once daily and at most two to three times daily, with adjusting dosing as indicated), although other patients may only require AAGP level be measured once every two to three days or possibly as infrequent as weekly, particularly if their co-morbid clinical condition has stabilized adequately. In one embodiment, each dose or the total daily dose is adjusted by applying a predetermined linear relationship between Dose and AAGP levels, such as: Dose (µg/kg)=m*[AAGP (µg/mL)]+b, where the target $C_{pfree}$, and the linear relationship between Dose and AAGP levels (slope (m), and y-intercept (b)) are determined from clinical studies (see Examples 3 and 4, below).

Before describing such guided dosing in more detail, however, it is important to understand that many patients will benefit from treatment of ulimorelin as described herein without any measurement of AAGP levels being required. Thus, Example 5 shows, based on scintigraphic measurements of gastric emptying in normal human volunteers receiving IV administered ulimorelin, that therapeutic benefit can be achieved in the form of an improvement in gastric emptying T50 (the time it takes for the stomach to half empty from the meal, "GET50") at Day 1 and Day 4 of treatment with 80 µg/kg, 150 µg/kg, and 300 µg/kg ulimorelin administered TID. In particular, this was demonstrated using "liquid meal" emptying. The "food" typically provided to patients receiving enteral feeding is of a liquid or slurry form, similar to that provided in the healthy volunteers (HV) clinical study, and is therefore referred to herein as a liquid meal. This benefit, or acceleration of emptying as measured in this study in HVs, was greater than 30% on Day 1 and 20% on Day 4 for both treatment groups as compared with pre-dosing baselines.

Thus, in one embodiment, the present invention provides methods for improving gastric emptying in patients in need of such treatment, such methods involving administration of ulimorelin as described herein, and such methods resulting in GET50 improvements of at least 10, 20, 30% or higher on Day 1 of treatment and similar improvements after 2, 3, and even 4 or more days of continuous dosing. These methods are suitable for use in treating patients with EFI and other indications where the prokinetic effects of ulimorelin are therapeutically beneficial in the amounts and with the treatment regimens described herein. The study reported in Example 5 also showed meaningful improvements at GET25 (time to 25% empty) and GET90 (time to 90% empty), although few subjects reached this timepoint.

Moreover, the AAGP levels in these normal volunteers, compared to those of ICU patients generally (see Example 4 and other discussion hereinbelow) show that most patients, given the degree to which ulimorelin provides demonstrated and significant stomach emptying in normal volunteers at doses of 150 µg/kg and 300 µg/kg (and higher), and given that higher doses are tolerated, will safely benefit from standard dosing in ranges such as 80 µg/kg to 150 µg/kg; 150 µg/kg to 300 µg/kg; 225 µg/kg to 550 µg/kg; 300 µg/kg to 500 µg/kg; and 500 µg/kg to 600 µg/kg (BID or TID IV administration). However, if dosing in one of these "standard" ranges does not provide the desired benefit, then the physician can elect to proceed to one of the guided dosing methods of the invention.

An illustration of AAGP guided dosing in accordance with the invention follows. The percent of ulimorelin that is unbound in plasma, and therefore free to interact with its target, the ghrelin receptor, is dependent on the total plasma concentration of ulimorelin and the plasma AAGP concentration, such that as ulimorelin concentration increases in plasma at a fixed AAGP concentration, the free fraction also increases. Likewise, if AAGP concentration increases, such as in response to injury or illness, at a fixed total plasma concentration of ulimorelin, then the free fraction decreases. Consider then, a hypothetical patient with an approximately 3-fold higher AAGP level than "normal" (see Example 3) of 3000 µg/mL. This patient would have a substantially lower free fraction than a healthy subject with an AAGP concentration of 1000 µg/mL (this value is a "normal AAGP level" as previously defined in the scientific literature; see discussion below and in Example 4), for example, and therefore, a lower unbound (or free) plasma concentration, at the same dose. This subject might, therefore, have greater efficacy of ulimorelin (greater therapeutic benefit) if the dose were adjusted to accommodate a target $C_{pfree}$. If the theoretical $C_{pfree}$ target was 20 ng/mL and the relationship between dose and AAGP concentrations to achieve a $C_{pfree}$ of 20 ng/mL was Dose=0.6×[AAGP] (assuming the Y-intercept to be zero for this illustrative case), then the fictitious patient above with an AAGP level of 3000 µg/mL would require, for safe or efficacious dosing, a dose of 1800 µg/kg ulimorelin, compared with 600 µg/kg in the healthy subject with an AAGP concentration of 1000 µg/mL (see Example 3). While this theoretical calculation can be applied to any combination of: target Cmaxfree, efficacious dose in a subject with normal AAGP, and patient AAGP level, such guided dosing calculations will not be required for most patients, given the advantages of the dosing methods of the invention.

Various commercial assays recite a "normal range" of AAGP as ~50-120 (ng/mL). Healthy volunteers (HVs) evaluated in one study (see Example 5, below) have measured AAGP levels with a mean value of about 50, with standard deviation of about 10, and using these numbers, one can predict reasonably that ~70% of these HVs have "normal" AAGPs between ~40-60 using this assay. Moreover, analysis of AAGP levels in a study of ICU patients (see Example 4, below) at day 0 (baseline), 4, and 7 showed that the highest levels that could be measured, depending on the patient, could occur on any day, i.e., one could not predict when the highest AAGP levels would be reached for a specific ICU patient, Those of skill will appreciate that this complexity is of concern as peak AAGP levels have the most impact on Cmaxfree, the critical PK parameter.

Assuming 50 as the average "normal" AAGP level (adult subject not ill or injured), and using normal AAGP as the denominator, one can calculate the ratio of normal to peak value for each patient from this ICU patient study, the so-called "Multiple Ratio", Multiple Ratios may be similarly calculated, and conclusions can be reached, using other rational assumptions for the average AAGP level (i.e., 40). However, if one uses 50, then, for example, an AAGP of 90 is 1.8 times "normal" (90/50), while an AAGP of 320 is 6.4 times normal. For this particular study (see Example 4), an interim analysis showed that 27% of critically ill patients had AAGP level up to 1.9× normal; 62% up to 2.9×; and 94% up to 4.9×.

Those of skill in the art will appreciate that the accommodation of large dosing ranges can be prohibitive from a commercial or logistics perspective. The present invention arose in part from the discovery that certain set doses and dose ranges would adequately treat large segments of the intent to treat population. The analysis above, together with the efficacy data from healthy volunteers show that certain "set" doses, i.e., 150 µg/kg per administration (450 µg/kg/day), 300 µg/kg per administration, 500 µg/kg per administration, and 600 µg/kg per administration, can be used to treat large segments of the AAGP population without prior knowledge of AAGP levels, with a dose in the range of 300 µg/kg-600 µg/kg per administration (TID) being a very common dose, Conversely, higher doses (higher than 600 µg/kg) can be administered where AAGP levels are much higher than normal (see Example 4).

While the discussion above focuses on higher than normal AAGP levels, the present invention also addresses those patient populations where AAGP levels may be lower than normal. Such patient populations include infants, particularly prematurely born infants, sometimes referred to as "premies", who commonly have deficiencies in GI (gastrointestinal) function, including deficiencies that, in some cases, inhibit or impair required enteral feeding. The invention can be of benefit to these patients in need of treatment due to impaired GI function. One subset of premies that should especially benefit is the set of those whose present age is between ages (calculated from conception) 26-36 weeks. Premies younger than this sometimes need only trophic feeding amounts (and hence any intolerance to enteral feeding may not impair delivery of an amount of food which is felt to be sufficient by medical caregivers). Upon reaching 26 weeks, or at a different time when feeding goals are advanced beyond trophic feeds, EFI, if present, will inhibit reaching such goals and physicians may elect to prescribe a therapeutic to treat the EFI. Premies reaching >36 weeks may typically outgrow any EFI quickly due to overall GI tract development and functional maturation. In certain premies with EFI, the combination of beneficial effects offered by ulimorelin, notably both promotility and anabolic effects, will be advantageous versus benefits offered by other medications offering prokinetic effects only. Of course, ulimorelin can be used in combination with any other prokinetic medications in this (and other) indications of interest herein.

The scientific literature reports, in one study, that normal term infants have, at birth, levels of AAGP of approximately half the adult normal range (see AAPS PharmSci. 2002 March; 4(1): 19-26). In another study, AAGP levels in newly born normal term fetuses were, on average, approximately one third (15.3+/−4.7 mg/100 mL) of their mother's levels (49.6+/−6.5 mg/100 mL) (p<0.002) (see Clin Pharmacol Ther. 1981 April; 29(4):522-6). A study of AAGP in preterm neonates vs. infants vs. 18 year olds showed that AAGP levels increase significantly with increasing age (see Clin Pharmacol Ther. 1989 August; 46(2):219-25).

For some later term premies either born at or close to full term and thus born with, or, having developed subsequent to an earlier time of premature birth, roughly the typical one third to one half of the typical adult AAGP level, the resulting free fraction of drug from a given ulimorelin dose will be higher than in the adult by a similar inverse factor (i.e. roughly threefold higher if the former and twofold higher if the latter). As such, a safe and efficacious dose administered in accordance with the invention will be reduced by roughly the same factor as the relative AAGP reduction, such that if the adult dose were 300 µg/kg, then, adjusting specifically for AAGP, the dose would be roughly 100 µg/kg or 150 µg/kg, respectively. For a very early term premie born with essentially no AAGP, virtually all ulimorelin dosed would remain unbound (and thus active) and as such a safe and efficacious dose of ulimorelin would likely be in the range of 1/100-1/10 of the weight—based dose for a normal adult. Furthermore, as is typical for a drug dosed by weight in adults (µg/kg, for example, as with ulimorelin in the methods of this invention), a metabolic translational factor may be applied for some pediatric patients (including premature infants) that will act to increase the weight-based dose, i.e., if the dose in adults is 150 µg/kg, then in premies treated by physicians applying such a translational factor, the dose would be 1.5 to 10 fold higher (i.e. 225 to 1500 µg/kg dose in µg/kg); provided, however, that such dose would still need to be further adjusted downwards to account for the premie's having an AAGP level lower than for a normal adult, if such is the case. Those of skill in the art will recognize that such translational factors can be readily calculated using commercially available modeling software.

Given the potential variability in AAGP levels in premies, the increasing baseline levels as premies progress to the equivalent of full gestational age, measurement of AAGP and adjustment of ulimorelin dosing as provided herein can be used to ensure safe and effective dosing. Thus, an appropriate ulimorelin dose can be calculated from measured AAGP; the dose can be adjusted as frequently as hourly or daily in some premie patients but more typically, for most EFI patients, if measured at all, AAGP is measured once, or only once or twice per week for patients that stay that long or longer in treatment. For premies, the dose can range from as little as 1/100 of the adult weight-based dose to as much as one half that the adult dose; and, further, that, if a metabolic translational factor is used, the dose can be further adjusted upwards by 1.5-10 fold (dose in µg/kg).

As an illustrative example of all of the various embodiments of the invention in which the patient receiving benefit is on a nasogastric feeding tube or similar feeding device and the treating physician is concerned about EFI, the following is a description of a typical patient who could benefit by treatment in accordance with the invention. Such a typical patient may be admitted to an intensive care unit and be, as frequently the case, unable to eat on his or her own. This can be due to many different causes, including, as non-limiting examples, sedation, such as from medically-induced coma or sedating pain medication, delirium, or the presence of an endotracheal tube for the provision of mechanical ventilation. In typical practice, within the first 1 to 72 hours, or at a time when deemed acceptable by caregivers, a nasogastric or similar tube will be inserted into such a patient, through which a general liquid feeding formula will be delivered, either in boluses, as a continuous drip, or as an intermittent continuous drip possibly with boluses as well.

Typically, after a certain amount has been infused and typically after 4 to 8 hours if by continuous drip, a study will be conducted to determine the GRV of the amount provided, for which feeding will be interrupted. In some embodiments, a certain amount of time, such as approximately 30 minutes, will be allowed to elapse, and then gastric residual contents will be aspirated by syringe or similar method. Should the GRV (or other indicator of EFI) be deemed excessive in the caregiver's judgment, typically in excess of an amount between 200 to 500 mL or more, as a non-limiting example, then feeding will be suspended.

A certain amount of time will be allowed to elapse, and then typically the GRV (or other indicator of EFI) will be rechecked, with feeding having been restarted at the same or lower infusion rate in between, or with feeding on hold in between assessments. If GRV (or other indicator of EFI) is deemed sufficiently low (i.e., below or on the low end of the range above, for example), then feeding will be restarted. After a caregiver-determined number of GRV (or other indicator of EFI) readings are deemed excessively high, but often either one or two, the patient will be declared intolerant to enteral feeding, i.e., the patient may benefit from treatment of EFI, as provided herein.

Those of skill in the art will appreciate that various physicians will determine the need for therapeutic intervention for EFI in a variety of ways, and the ways listed herein are illustrative. For example, many physicians might take only a single GRV reading before diagnosing EFI and taking corrective action. Moreover, there are a variety of ways an individual physician may make a diagnosis of EFI without taking any GRV measurement, such as the observation of abdominal distension or vomiting, use of paracetamol absorption kinetic testing, use of scintigraphy, and others. The particular diagnostic methodology will often take into account the patient status; thus, for example, while GRV measurements are suitable for comatose patients, other methods, e.g. scintigraphy, are more appropriately done in on patients who are ambulatory. Those skilled in the art will appreciate that despite the variability in physician practice patterns and preferences with regard to making an EFI diagnosis, the underlying motility disorder, impaired gastric emptying, is common to all such patients and as such the therapeutic promotility benefit of ulimorelin will apply generally.

In particular, GRV measurements provide information about how much food remains in the stomach, but another way to diagnose EFI involves gastric emptying measurements made with scintigraphy (see Abell et al., Am. J. Gastroenterol. 2008; 103:753-763, incorporated herein by reference). Scintigraphy was used to measure gastric emptying in the HV study reported in Example 5 but is not ideal for clinical practice in the ICU population because of difficulty implementing it in that setting. Furthermore, those skilled in the art will appreciate that a drug which accelerates gastric emptying times as measured by scintigraphy in healthy volunteers will similarly accelerate or restore impaired, delayed, or stopped, gastric emptying in patients, including those who are critically ill, whether or not scintigraphic measurement is made of those patients, and that furthermore there are other measures which can serve as a similarly valid proxy of gastric emptying activity, such as the measurement of the amount of enteral feeding which a medical caregiver is able to provide and a patient is able to tolerate over a defined period of time.

Thus, while the diagnosis of EFI may be made without use of GRV measurement, including simply on symptoms alone, such as nausea or vomiting, distended abdomen, or others of similar GI relevance; or inferred from other measurements, such as gastric emptying scintigraphy, there remains a need for better treatment methods, and the need is relatively large: a recent study cites a prevalence of roughly 30% of ICU patients being labeled as having EFI (see Gungabissoon et al.; JPEN J Parenter Enteral Nutr 2014 Mar. 17).

In other embodiments of the invention, after the EFI is resolved or enteral feedings have been stopped, the physician may continue administration of ulimorelin at the doses provided herein, and using qD, BID, or TID administration to provide continuing anabolic benefit to the patient. In treating EFI, the treating physician may desire both the promotility effects of the drug and the anabolic benefit. These combined features, which are particularly beneficial for critically ill EFI patients and which accrue from use of a properly and ideally dosed and administered (IV) ghrelin agonist, as provided for ulimorelin herein, provide a "prokinetic plus" benefit to patients and such treatment is thereby differentiated from any therapeutics that offer only one or the other benefit. As demonstrated in the examples below, ulimorelin dosed in accordance with the invention to normal subjects causes growth hormone spikes, which should have a beneficial therapeutic effect in patients in a catabolic state requiring treatment.

Once the caregiver has determined a need to treat, the patient will then be administered ulimorelin via IV administration on a TID schedule at a dose of 80 µg/kg per administration to no more than about 1200 µg/kg per administration (240 to 3600 µg/kg/day). In many embodiments, each dose will be in the range of 300 µg/kg per administration to no more than about 600 µg/kg per administration (900 µg/kg/day to 1800 µg/kg/day), with many patients receiving benefit at doses in the range of 500 µg/kg per administration to no more than about 600 µg/kg per administration (1500 to 1800 µg/kg/day). Patients receiving doses higher than 600 µg/kg TID will have AAGP levels that are unusually high, even for being in the intent to treat population. Most patients will receive a set dose in the range of 500 µg/kg to 600 µg/kg per dose administered TID for EFI and optionally qD or BID, as well, for anabolic effect. In other embodiments, patients will benefit from receiving doses of 300 µg/kg to 1200 µg/kg per administration. Treatment will be continued for at least a day, typically at least two consecutive days and often continuing for at least four days or longer. In some instances, treatment will be administered daily for the length of the patient's subsequent stay in the ICU. For some patients, AAGP blood levels will be determined and used to guide dosing or dose adjustment.

Patients treated for EFI should receive ulimorelin TID. In EFI patients where TID administration is not optimal, whether due to side effects or diminished efficacy as a result of tachyphylaxis or care provider convenience or preference, the drug may be dosed by BID administration at a dose in the ranges provided above but administered BID instead of TID (160 µg/kg/day to 2400 µg/kg/day). That said, while BID administration can be practiced with any patient for whom the treating physician believes such administration superior to TID for any reason, BID administration methods, if used at all, are more suited for patients not being treated for EFI, i.e., where the anabolic and/or anti-cachexic effects are the primary benefits desired. In various embodiments of the invention, for example, a patient being treated for EFI may continue to receive ulimorelin after EFI has resolved to provide anabolic benefit. In this post-EFI treatment scenario, dosing may be qD, BID, or TID, as the physician elects, and the individual doses will be in the ranges provided above for TID, e.g. 80 µg/kg to 1200 µg/kg.

The invention, having been described in summary and detail above is now illustrated, without limitation, in the following examples.

Example 1 shows that human ghrelin blood levels vary in a pulsatile manner, typically rising with three daily distinct, sharp peaks prior to typical times of meal-seeking behavior and declining post-prandially, in normal individuals. The methods of the invention provide superior efficacy over prior methods due, at least in part, to employing q8H (TID) administration, which mimics this naturally occurring cycle of the normal human ghrelin levels (with three spikes a day occurring at mealtimes, e.g., about every four to six hours). In addition, TID administration can compensate for a short ulimorelin free drug half-life (serum total drug half-life is ~15 hours which mostly consists of bound (inactive) drug).

Example 2 shows that ulimorelin is extensively bound to AAGP, an acute phase reactant protein that binds ulimorelin, reducing the free plasma concentration $C_{pfree}$. AAGP levels have been often reported as substantially higher, and significantly more variable, in sick or injured patients. AAGP levels can vary over the course of therapy, resulting in lower or higher free plasma concentrations of ulimorelin, with corresponding lesser or greater efficacy.

Example 3 provides a method for adjusting the dose of ulimorelin based on measured AAGP levels in patients, achieving a target $C_{pfree}$ at Tmax (Cmaxfree) to maximize efficacy.

Example 4 describes how samples from ICU patients can be used to estimate an expected range of AAGP in a target population and reports results from such testing.

Example 5 describes clinical trials that have been or could be conducted to demonstrate that the methods of the invention are safe and efficacious in the treatment of EFI, and includes results from administering ulimorelin to HVs (shown to have normal AAGP levels) at doses in the ranges specified herein.

The results and accompanying discussion in the Example and Figure legends above are applicable to all aspects of this disclosure and demonstrate that treatment of ulimorelin in accordance with the invention provides therapeutic benefit by improving gastric emptying, ensuring the Cmaxfee is in the desired therapeutic window, and increasing GH levels. The data and analysis shown in Examples 4 and 5 and provided herein demonstrate that the therapeutic effects of ulimorelin at the doses described and the AAGP variability in the population as a whole and in the intent to treat population are such that significant numbers of ICU patients will benefit from the standard dosing regimens described herein (i.e., dosing at 150 µg/kg, 300 µg/kg, 500 µg/kg, or 600 µg/kg BID or TID, depending on indication and presenting patient attributes) without measuring AAGP levels.

Other indications that can be treated in accordance with the invention include but are not limited to both upper and lower GI motility conditions as well as conditions of excess catabolism or inadequate anabolism, inadequate food intake for any reason, including cachexia, both in patients who are critically ill, and those who are not critically ill but are in an acute care facility or chronic care facility and require an intravenous medication. Such conditions include enteral feeding intolerance; gastroparesis, including but not limited to patients with diabetic gastroparesis, neurogenic gastroparesis, idiopathic gastroparesis, drug-induced gastroparesis, viral gastroparesis, obesity-induced gastroparesis, Ogilvie's syndrome, non-toxic megacolon, pseudoobstruction, gastroparesis or ileus or megacolon associated with neurologic impairments including Parkinson's disease or multiple sclerosis or mental retardation or spinal cord injury, post-operative ileus, including but not limited to prolonged post-operative ileus in which typical timelines for recovery from a post-operative ileus state, such as 3 to 5 days, are not met, other conditions of gastrointestinal dysmotility as either primary or secondary conditions, for the latter of which one non-limiting example is pancreatitis-induced ileus.

Those of skill in the art upon contemplation of this disclosure and that of U.S. Pat. No. 7,491,695 (RE 42,624); U.S. Pat. Nos. 8,349,887; and 8,450,258, incorporated herein by reference, will appreciate that the present invention includes methods as described in these patents but in which ulimorelin (or therapeutically equivalent formulations of molecules with similar activity) is administered IV TID in doses as described herein, e.g. 250 µg/kg to 600 µg/kg, in many embodiments.

Accordingly, the present invention is also directed to ulimorelin for use in the treatment or prevention of the indications as mentioned in the dosage regime as disclosed herein and the claims.

These and other aspects and embodiments of the invention may be better appreciated after consideration of the following examples.

EXAMPLES

Example 1—Human Ghrelin Release

Figure 2:
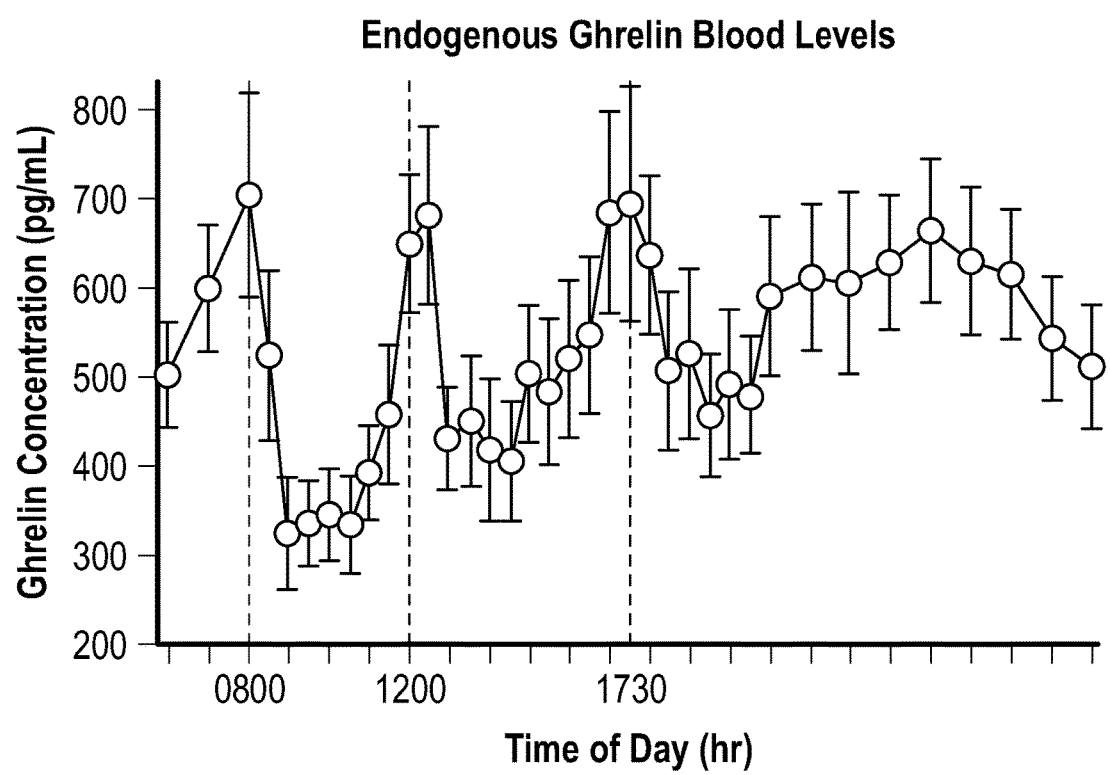
FIG. 2 is graphically presented data showing that endogenous ghrelin blood levels are pulsatile, rising sharply prior to eating thrice daily and declining post-prandially, as discussed in Example 1.

Endogenous ghrelin blood levels are pulsatile. Ghrelin rises sharply prior to eating and declines post-prandially. This happens about three times a day in healthy individuals (see Cummings et al., Diabetes 50:1714-1719, 2001). With reference to FIG. 2, average plasma ghrelin concentrations over a 24 hour period in 10 human subjects consuming breakfast, lunch, and dinner is shown. Plasma samples were collected and tested at the time indicated by dashed lines, namely, 0800, 1200, and 1730 [FIG. 2 adapted from: A Preprandial Rise in Plasma Ghrelin Levels Suggests a Role in Meal Initiation in Humans, Cummings et al., supra].

Example 2—Binding to AAGP

Figure 3:
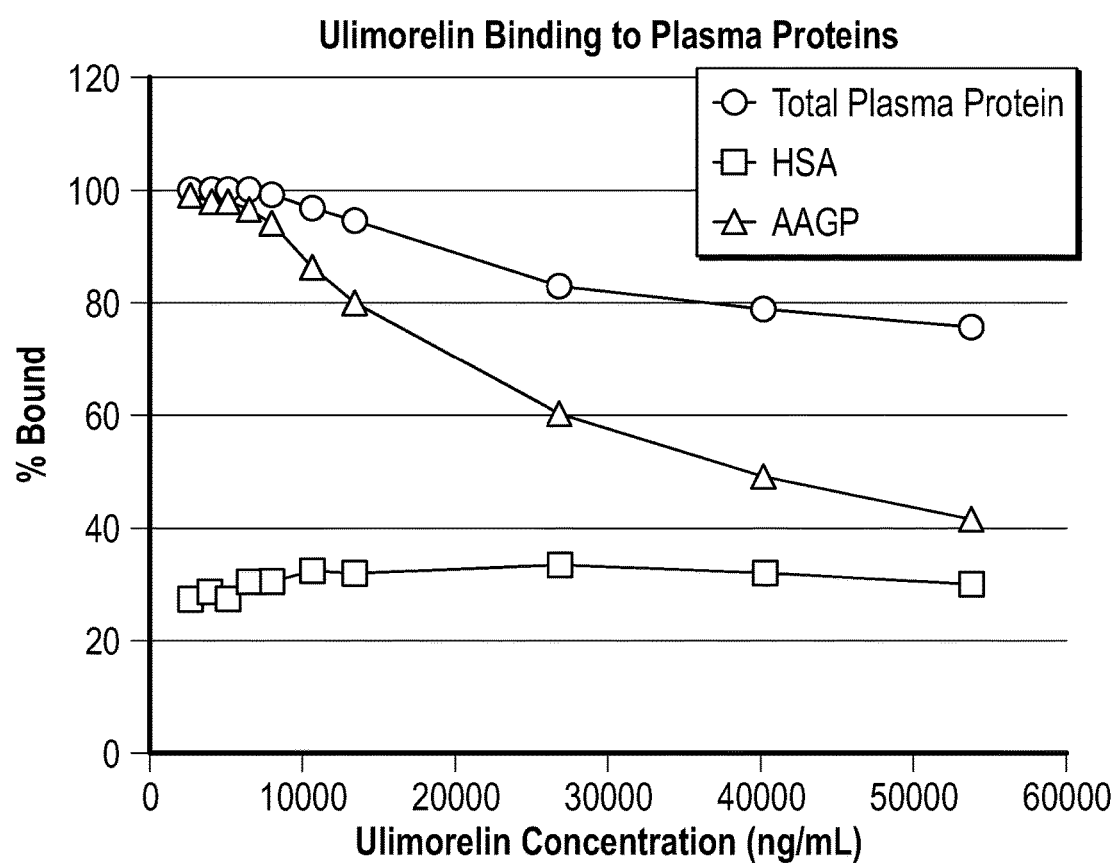
FIG. 3 is graphically presented data showing ulimorelin binding to total plasma proteins, purified human alpha 1-acid glycoprotein (1000 µg/mL AAGP) and albumin (4% w/v HSA), as discussed in Example 2.

As shown in Table 1 and FIG. 3, ulimorelin is extensively bound (approximately 95 to 99%) to human plasma proteins at concentrations at and below 15 µM, which encompasses the plasma concentrations observed in the clinic. AAGP was identified as the major binding protein for ulimorelin in human plasma, with human serum albumin (HSA) being a minor contributor to the overall plasma protein binding. In vitro, the fraction of ulimorelin bound to AAGP ranged from >99% to <50% at ulimorelin concentrations ranging from 5 to 100 uM and at an AAGP concentration of 1 mg/mL, representative of the normal range in healthy humans. The fraction of ulimorelin bound to HSA was approximately 30% and was independent of ulimorelin concentration across the concentration range (5-100 µM) tested.

TABLE 1

Ulimorelin Binding to Total Plasma Proteins, Purified Human Alpha 1-Acid Glycoprotein (1000 µg/mL AAGP), and Albumin (4% w/v HSA).

| | % Bound | | |
|---|---|---|---|
| Ulimorelin (uM) | Total PPB | 1000 µg/mL AAGP | 4% HSA |
| 5 | 99.8 | 99.7 | 27.6 |
| 7.5 | 99.8 | 99.4 | 28.9 |
| 10 | 99.7 | 98.8 | 27.7 |
| 12.5 | 99.5 | 97.2 | 30.5 |
| 15 | 99.1 | 94.8 | 30.8 |
| 20 | 97.1 | 86.7 | 32.5 |
| 25 | 94.7 | 80.5 | 32.4 |
| 50 | 83 | 60.3 | 33.3 |
| 75 | 79.1 | 49.5 | 32.4 |
| 100 | 75.8 | 42.2 | 30 |

Example 3—Adjusting Dose by AAGP Level

Figure 4:
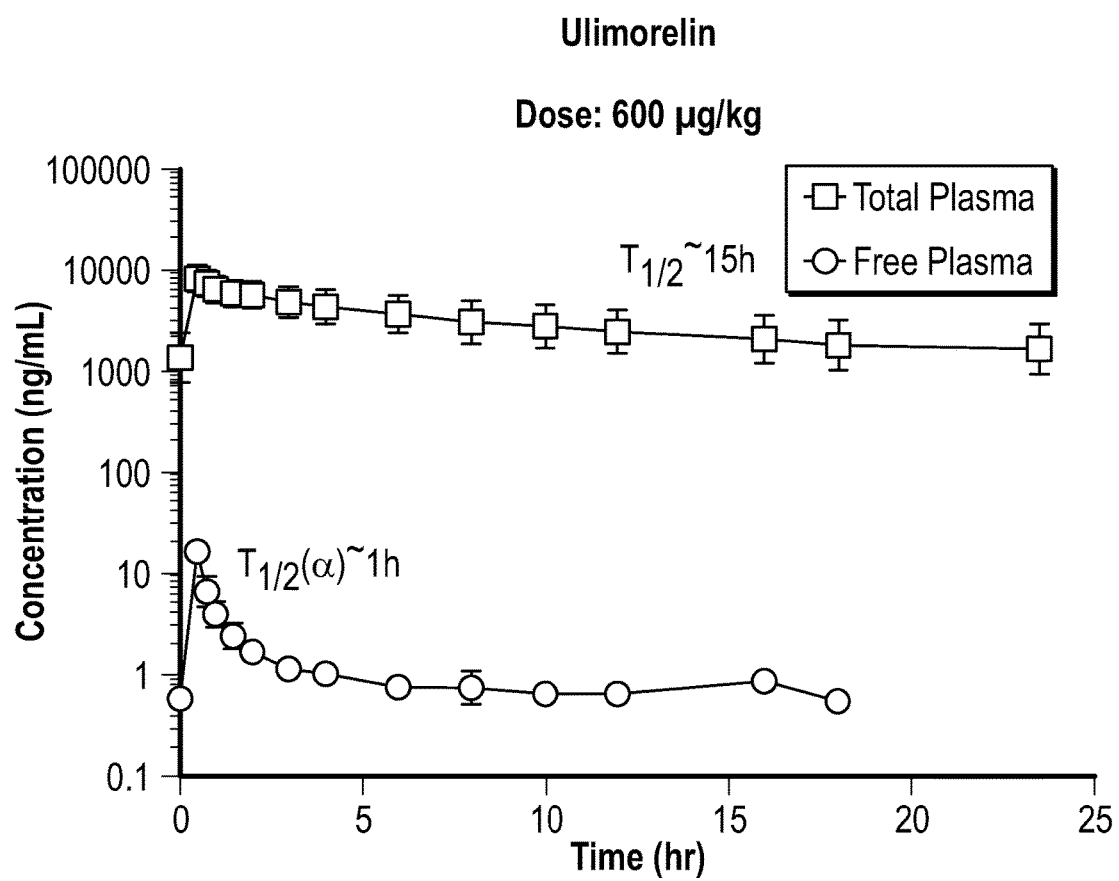
FIG. 4 is graphically presented data illustrating how total and free plasma concentrations measured in healthy subjects following a 30 minute IV infusion of 600 µg/kg ulimorelin may track one another, as discussed in Example 3.
Figure 5:
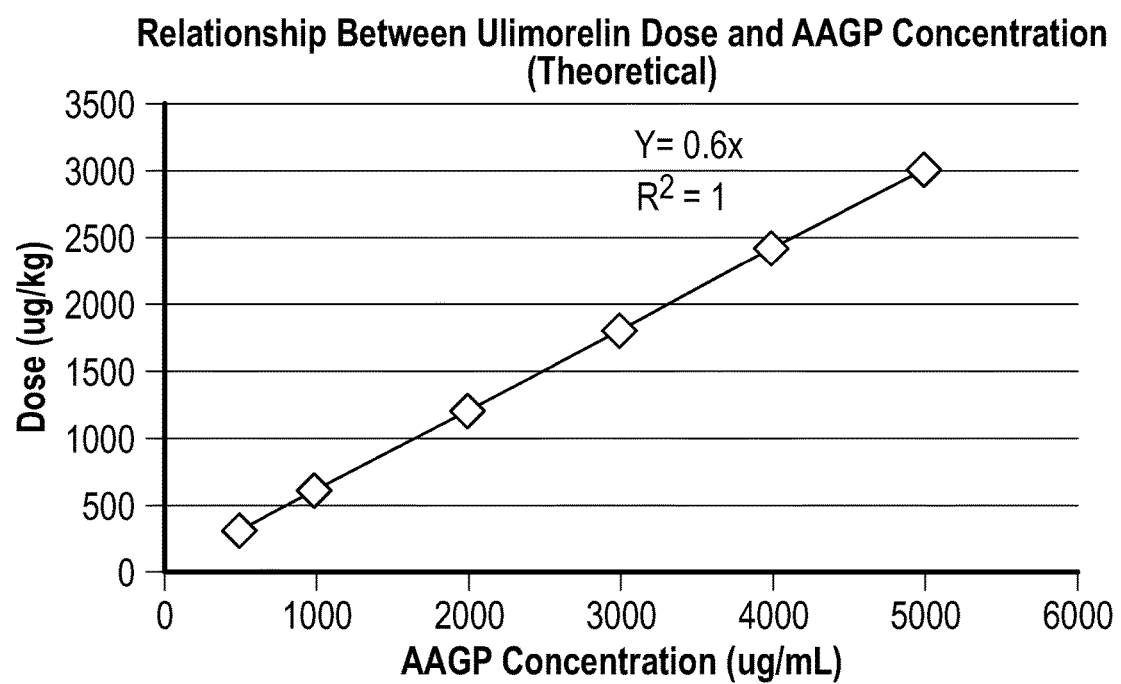
FIG. 5 is graphically presented data illustrating a theoretical relationship between dose and AAGP concentrations enabling one to predict the dose needed to maintain a $C_{pfree}$ of 20 ng/mL, as discussed in Example 3.

This example illustrates methods of the invention in which an EFI patient's serum AAGP concentration (level) is measured and used to adjust dosing of ulimorelin based on a target $C_{pfree}$. $C_{pfree}$ at $T_{max}$ (Cmaxfree) was determined to be about 10-25 ng/mL at 600 µg/mL from dialysis studies of plasma from healthy volunteers enrolled in the Thorough QT (TQT) study (Table 2 and FIG. 4), so 20 ng/mL is used here as a theoretical target $C_{pfree}$ (actual value can be determined in clinical studies in an EFI population). Because the free fraction is dependent on the ratio of total drug to AAGP levels, the total dose can be adjusted to maintain the desired ratio, and thus $C_{pfree}$. The theoretical plot in FIG. 5 illustrates that dose varies linearly with AAGP concentrations for a given $C_{pfree}$. In this "ideal" example, the factor to adjust dose is: Dose (µg/kg)=0.6*[AAGP (µg/mL)]. This is just an example; the actual relationship can be determined by clinical studies in EFI patient populations and subsets of those populations, as described in Example 4.

The relationships between both total and free drug levels to AAGP levels in healthy volunteers was established across dose levels in the Phase 1 study described in Example 5. Furthermore, the increase in Cmaxfree versus dose was established to be exponential and was predictable. In healthy subjects, Cmaxfree at 150 µg/kg, one of the doses deemed both efficacious for gastric emptying and safe, the relationship between Cpfree at Tmax (Cmaxfree) drug level and AAGP level could be described as Cmaxfree=−0.099*AAGP+6.22 ($R^2$~0.7). This confirms that, as AAGP levels change, the resulting desired Cmaxfree can be determined, which when taken together with the dose proportionality relationship, between dose and Cmaxfree, permits the estimation of any required dose or dose adjustment. As will be described in Example 4 in connection with Multiple Ratios (patient AAGP versus normal AAGP), these fundamental relationships (Cmaxfree versus dose and Cmaxfree versus AAGP level) confirm that, in humans, at the doses described herein as efficacious in the treatment of EFI, e.g., 80 µg/kg to 1200 µg/kg, given a roughly constant ratio of ulimorelin to AAGP, a roughly constant free fraction is maintained. For example, if the patient's Multiple Ratio is 4, then to acheive approximately the same Cmaxfree achieved by a dose of 150 µg/kg in a person with normal AAGP, the adjusted patient dose would be 150 µg/kg×4, or 600 µg/kg. Further assessment of the actual Cmaxfree achieved in any given patient can be determined and the dose therefore, adjusted if needed, accordingly.

TABLE 2

Mean Total and Free Pharmacokinetic Parameters in Healthy Subjects Following a 30 Minute IV Infusion of 600 µg/kg Ulimorelin

| | |
|---|---|
| Total $C_{max}$ (ng/mL) | 7900 |
| Free $C_{max}$ (ng/mL) | 16 |
| Total $t_{1/2}$ (hr) | 17 |
| Free $t_{1/2}$ (hr) | <4 |

Example 4—Determining Reference AAGP Levels in Various Healthy and Patient Populations and Correlation to Efficacious Dosing This example illustrates how one can conduct studies to determine AAGP levels in various populations including both healthy volunteers with normal levels as well as particular intent to treat populations to determine reference levels that can be used to translate ulimorelin efficacy results from one population to another and to predict optimal dosing levels. In this example, analyses of AAGP levels in various ICU (or other critically ill) patient populations compared to AAGP levels in normal healthy individuals (see Example 5) as well as to published reports of AAGP levels in various populations were conducted. The discussion of the results demonstrates that the doses described herein should be therapeutically effective in the majority of EFI patients, despite the variability of AAGP levels in the ICU target population.

Plasma samples collected during a prior clinical study of ICU patients with heterogeneous and broadly representative admitting diagnoses (see N Engl J Med 2013; 368:1489-1497) were analyzed to assess the variability of AAGP in this sample set. These patients are representative of those in the intent to treat patient treatment population, although patient samples were included regardless of whether the patient was receiving enteral feeding, for the methods of the present invention. The assessed variability is used, for illustrative purposes, to demonstrate that the fixed doses (i.e., 150 µg/kg, 300 µg/kg, 500 µg/kg and 600 µg/kg per administration) described herein can be used to treat a significant proportion of patients, as well as provide guidance regarding when, whether, and how often to measure AAGP levels in specific patients prior to administering or continuing to administer the drug to ensure safe and most efficacious dosing. The results reported here can be used to guide treatment decisions, as discussed below; moreover, this methodology can be used to analyze other groups of patients (including EFI patients) to provide recommended doses and treatment regimens for any patient population of interest to the treating physician.

The 153 samples (from 63 patients) used in one of the studies (from the published REDOXS study) were samples from ICU patients with admitting diagnoses including, among others, pneumonia (infectious and aspiration), neoplasm, drug overdose, trauma, various gastrointestinal disorders, sepsis, cardiopulmonary illness (e.g. cardiogenic shock, cardiomyopathy, acute myocardial infarction, respiratory arrest, and, congestive heart failure), as well post-operative patients who had undergone various types of surgeries. In addition to the REDOXS study, approximately 80 plasma samples (from 29 patients) collected during a prior clinical study of burn patients in the ICU (the RE-ENERGIZE study) were analyzed in a second study to assess the variability of AAGP in this specific patient treatment population Samples analyzed for AAGP in the REDOXS study were drawn at study entry (typically shortly after ICU admission, i.e., "baseline"), as well as day 4 and day 7. Samples from the RE-ENERGIZE study were taken at days 4, 7, 14, and 21. Some samples (and therefore data) for various timepoints were missing for patients in both studies. All samples were analyzed in a commercial laboratory (LGC, UK) using Randox Laboratory, Ltd.'s alpha-1-acid-glycoprotein (AGT) kit (Cat. No. AG2472).

To assess variability and trends in AAGP levels in these patient samples, the data were analyzed to determine high and low values as well as whether an individual patient's AAGP levels varied in a predictable fashion during their ICU stay. From all patient samples at all time points measured, the lowest AAGP level was 44, from a sample obtained at the baseline timepoint. The next lowest were two readings of 45 and 46, both from samples drawn at day 7. The lowest reading from a Day 4 sample was 56. From all samples at all time points, the highest AAGP was 390, a Day 4 reading. The highest baseline reading was 291. The highest reading from a Day 7 sample was 360. The variability of readings was striking and unpredictable with regard both to extent and timing of elevated readings, when seen, as well as with regard to the presence of unexpectedly low values that were closer to values seen in healthy volunteers (Example 5). Generally, however, the majority of patients in each of the distinct admitting patient groups (i.e., post-surgical, sepsis, neoplasm, as examples) had elevated AAGP levels (relative to a "normal" range of ~40 to 60 mg/dl).

The trends in the data generally demonstrated that ICU patients had markedly higher AAGP levels than healthy volunteers and that certain patients, particularly those with persistent medical illness, e.g., infectious disease, and those patients recovering from surgery, as examples, might reasonably be expected to have significantly elevated levels. For post-surgical patients, peak levels were typically seen in the Day 4 or Day 7 samples, consistent with the expectation that, as an acute phase reactant, AAGP should increase after an inflammatory triggering event (like surgery) and remain high or even increase for so long as the inflammatory condition exists. Interestingly, patients who have impaired ability to mount an inflammatory response, including due to persistent overwhelming illness, may not have elevated AAGP levels.

The data from these two studies was compared to AAGP levels from samples collected from healthy volunteers enrolled in a Phase 1 study of ulimorelin safety, PK, and PD effect (see Example 5), from Day 1 and Day 7 (again, not all patients provided samples at all time points). At least 70 samples from over 30 patients were tested. The range of AAGP values was 32-77 mg/dL (e.g. ~30 to 80 mg/dL), with mean and standard deviation of approximately 50+/−10 mg/dL.

To demonstrate the significance of these data to the methods of the invention, one can compare the AAGP values from REDOXS and RE-ENERGIZE patients and from healthy volunteers by calculating the ratio of a given patient's AAGP level at a given time to a derived value for a normal AAGP level. One way to make this comparison is to use the patient's AAGP level as numerator and normal level value as denominator, such a fraction is referred to herein as the "Multiple Ratio." The Multiple Ratio shows how many fold over (or under) normal a given patient AAGP reading is. Further, by knowing the distribution of Multiple Ratios obtained using samples intended to minor the intent to treat population, as is done in this example, one can predict the likelihood, distributionally, that a given patient at a given time will have such a ratio (be it 1, i.e., a normal level, or a lower or higher value, depending on whether the patient AAGP level is lower or higher than normal, respectively, and thus predict the likelihood that Cmaxfree for said patient from a given ulimorelin dose will be different from that typically seen in a healthy normal person who receives the same dose.

To illustrate this more readily for the artisan of ordinary skill, one can define ranges of Multiple Ratio, such as, for example, 1 to <2. Such ranges may be standalone and so predict the likelihood that a given patient will have an AAGP level in that particular range (e.g. a range of 1 to <2 or a range of 2 to <3), or, more usefully for purposes of the present invention, cumulative, eg 1 to <3 or 1 to <4. If the value for normal AAGP level is set at 50 mg/dL (as determined in the healthy volunteer study), then Table 3 provides the cumulative percent of the ICU population with AAGP values in the specified range.

TABLE 3

Cumulative Percent of Patient Population
with AAGP Levels in Each Multiple Ratio

| Ranges of Multiple Ratio (ICU/Normal) | Cumulative % ICU Population with a Multiple Ratio between the corresponding values listed |
|---|---|
| <1 | 2 |
| 1 to <2 | 27 |
| 1 to <3 | 62 |
| 1 to <4 | 87 |
| 1 to <5 | 94 |
| 1 to <6 | 99 |
| 1 to >6 | 100 |

AAGP levels dictate how much of a given ulimorelin dose remains in unbound (free) form—the form that exerts the desired pharmacologic effect for EFI. The higher the AAGP, or stated differently but with the same implication, the higher the Multiple Ratio, the lower the proportion of total drug administered that will be in free form at a given dose level (i.e., therapeutically active), and in particular, the lower Cmaxfree will be (with the opposite of these true as well). The percentage of patients from these two ICU studies that fall into a range of Multiple Ratios should be similar to that for the general ICU intent to treat population, and the table above can be used to predict that percentage. Importantly, this same process can be used for any given "normal" AAGP value; thus, while this example uses 50 as the normal value, similar calculations can be made using another reasonable value, i.e., 40 to 60 mg/dl).

In Table 3, the various ratios shown that fall into each resulting cutoff range correlate with the likelihood that any given ICU patient will receive maximal therapeutic benefit from ulimorelin dosed at a particular dose (for EFI or follow on anabolic effect). For example, given, from the above table, that 62% of patients studied had Multiple Ratios in a cumulative range between 1-2.9 (i.e. 1 to <3), for example, the treating physician can reasonably infer that the likelihood that any specific patient under his or her care has an AAGP at a given time within this same cumulative Multiple Ratio range is also about 62%.

Data collected and analyzed as above combined with the Cmaxfree data (presented in Example 5) from healthy volunteers receiving ulimorelin show that, in fact, with Multiple Ratios as high as 3, the Cmaxfree from a dose in the 500 µg/kg to 600 µg/kg range is maintained above 1 ng/mL. As such, for this dose, the likelihood of achieving maximal therapeutic benefit in treating ICU EFI is very high. For non-ICU patients expected to have generally lower AAGP, the odds will be even more favorable. Given that a dose in the 500 µg/kg to 600 range should generally produce a Cmaxfree above the minimally efficacious level (while also being safe to administer) for any AAGP value within the Multiple Range 1-2.9, the physician will know that there is a 62% likelihood of achieving an efficacious (and safe) Cmaxfree when administering this dose without the need to know the specific patient's AAGP level. Furthermore, as data demonstrate that sufficient therapeutic benefit for treating EFI may accrue to a patient whose Cmaxfree simply remains above the minimally efficacious level, as long as the Cmaxfree-lowering effect of a given AAGP elevation (i.e. a given Multiple Ratio>1) does not cause Cmaxfree generally to go below this minimally effective level, then the dose of ulimorelin will be sufficiently effective to achieve therapeutic goals.

Those of skill in the art, upon contemplation of this example and the data and analysis presented herein, may appreciate that, prior to the present invention, it was impossible to predict with any confidence what Cmaxfree values would result from administering ulimorelin to an ICU patient, even if that artisan were focused on Cmaxfree instead of total drug levels. The scientific literature reports a wide variety of "normal" and elevated AAGP levels, and the "normal" levels reported typically show 50 mg/dL at the low end of the normal range (or even below); for example, the Randox assay reports a normal range of 50-120 mg/dL. However, the analysis here shows that, in a carefully conducted study, normal levels are relatively tightly centered about 50 mg/dL, allowing one to predict with confidence, given the Cmaxfree and gastric emptying data presented in the following example. Even if one were to select a different "normal" value, either arbitrarily or from findings of another study, one can use similar analyses to demonstrate that the doses described herein, particularly doses in the 150 to 600 µg/kg range, should be efficacious in a significant percentage of the intent to treat population. For example, if one assumes a normal value of 40 and does the same calculations as above, then one would expect that at least ~40% of patients will have a Multiple Ratio of 1 to 2.9 and so respond favorably to the doses described herein. Further, as one uses higher values for normal AAGP level, e.g. 60, and applies them to this data set, the percentage goes up (i.e., 80% of patients would be expected to have a Multiple Ratio of 1 to 2.9), meaning even more patients benefit from standard dosing, i.e., in the 150 µg/kg to 600 µg/kg range TID. These estimates are conservative, but it is also likely that patients with Multiple Ratios as high as 4 or higher will respond favorably to the doses described herein, without adjustment, but should adjustment be required, then the discovery from Example 3 can be applied to this subset of the population.

Based on the results reported herein, albeit from a limited population study of healthy volunteers, one may conclude that the definition of "normal" AAGP is lower than that cited in the literature, and is, instead, generally 40-60 mg/dL, with mean 50 mg/dL (as measured by the Randox assay cited herein). All values obtained in this healthy volunteer population study were between ~30-80 mg/dL. Based on similarly useful but limited population studies of patients in the REDOXS and RE-ENERGIZE studies (and as measured by that same Randox assay), it is clear that the large majority of the intent to treat population is likely to have elevated AAGP levels. Indeed, and specifically for purposes of this particular analysis, when using 80 mg/dL as the upper limit of normal for AAGP level, one could predict that 87% of patients in the intent to treat population will have AAGPs above normal and up to 300 mg/dL, a level which is unusually high. Therefore, even with these few and limited studies, one of skill in the art, upon reading the disclosures herein, will conclude that a significant percentage of ICU EFI patients will derive therapeutic benefit from standard dosing in the range of 500-600 µg/kg TID.

The power of this analysis and the high percentages it predicts provide a treating physician with a clear path to a therapeutically effective dose for any given EFI patient, as well as methods for safely increasing or decreasing dosing for those patients that do not respond as favorably as expected after initial treatment, as is illustrated in Example 6. First, however, the results demonstrating ulimorelin's therapeutic window, significant gastric emptying effects, and growth hormone level increases when dosed in accordance with the invention are presented in the following example.

Example 5—Clinical Study Results

A randomized, double-blind, placebo-controlled, single and multiple ascending IV dose (SAD and MAD), sequential-group study to assess the safety, tolerability, PK, and PD of ulimorelin in healthy subjects was initiated and conducted as follows. Healthy male and female volunteers aged 18 to 55 years participated in the trial. The objectives of the trial were to: evaluate the safety, tolerability, and PK of single and multiple ascending IV doses of ulimorelin at higher doses than in prior studies; valuate the PD of single and multiple ascending IV doses of ulimorelin, assessed by change in gastric emptying and growth hormone levels; and explore the relationship between AAGP levels and total/free ulimorelin plasma concentrations. Three cohorts were enrolled in a crossover design from the SAD to the MAD part of the study. The doses studied were SAD: 600, 1200, and 900 µg/kg and MAD: 300, 150, and 80 µg/kg q8H for seven days.

The following endpoints were measured: safety, PK (total and free ulimorelin concentrations), AAGP levels, and PD (gastric emptying by scintigraphic imaging (during the MAD part only) and growth hormone levels). This study was expected to demonstrate that dosing ulimorelin in accordance with the invention is safe and effective in promoting gastric emptying, and it did.

The quantitative composition of the drug product "intermediate" (while the vial is the unit dose form; the final drug product is delivered by infusion) is as follows (for a 10.5 mL vial): 21 mg ulimorelin hydrochloride monohydrate as free base, 6.3 mg glacial acetic acid, 504 mg of anhydrous dextrose, sodium hydroxide (1 M) q. s. to pH 4.5, and water for injection (WFI) q.s. to 10.5 mL. DPI was diluted into 5% dextrose in an IV bag under aseptic conditions for administration. All infusions occurred over 30 min, with volumes and concentrations adjusted to permit achieving the nominal dose for each subject in each dose group.

While single doses up to 1200 µg/kg and multiple doses up to 300 µg/kg were safe and well tolerated, a dose-related reduction in heart rate was observed, which, while not meeting the criteria for an adverse event (AE), suggested that bradycardia could occur at higher doses. Dose limiting toxicity was not achieved in the SAD part of the study, but protocol-defined stopping criteria as defined as a moderate AE in the same SOC (system organ class) in at least 2 subjects, specifically infusion site irritation, was achieved at 300 µg/kg q8H. At the doses studied, mean Cmaxfree ranged from about 1 to 79 ng/mL.

Figure 6A:
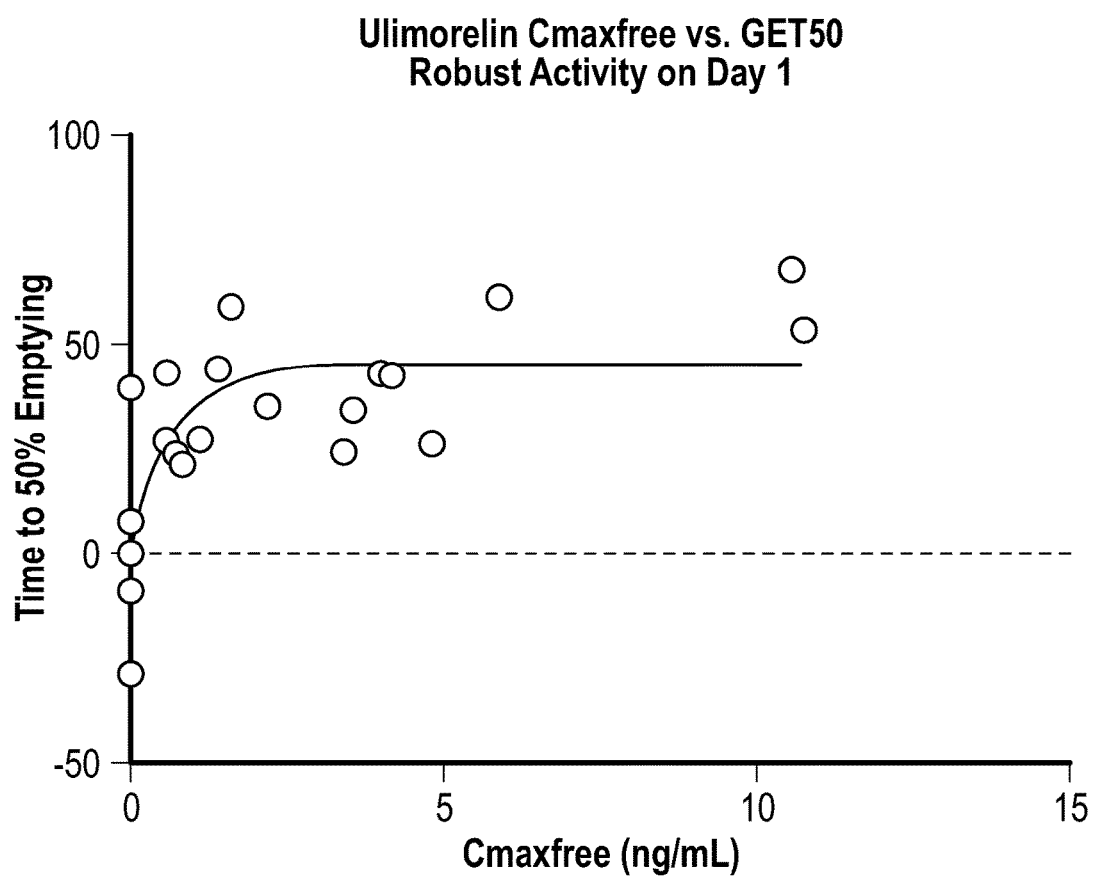
FIGS. 6A and 6B present graphical data showing Cmaxfree (Cpfree at Tmax, the time at which the maximum Cpfree is observed) vs efficacy as measured by gastric emptying in healthy volunteers (see Example 5) at Day 1 and Day 4 (parts A and B, respectively).
Figure 6B:
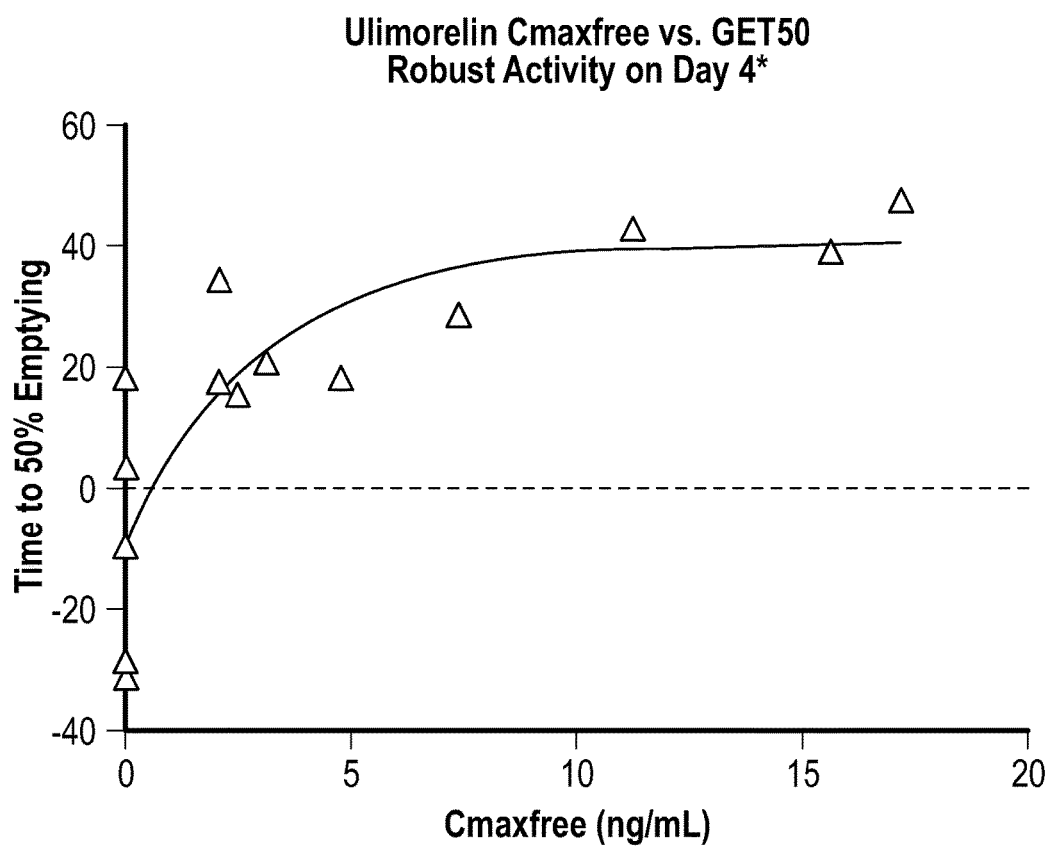

With reference to Table 4, gastric emptying, as measured by the time it takes to empty 25% (T25%, aka GET25) and 50% (T50%, aka GET50) of the stomach contents, was improved at doses ranging from 80 µg/kg to 300 µg/kg q8H, meeting statistical significance at 150 µg/kg and 300 µg/kg on Days 1 and 4 (statistical tests were not performed at 80 µg/kg). In various embodiments of the invention, the doses administered are in a range described herein that provides for free ulimorelin levels in the particular subject of interest of greater than about 0.5 to 1 ng/mL and less than about 125 ng/mL. PK-PD modeling of Cmaxfree versus gastric emptying (T50%) supports the conclusions that robust activity occurs at Cmaxfree levels of about 0.5 to 1 ng/mL on Day 1, and 3 ng/mL or more on Day 4. PK-PD is well described by an Emax model with maximum effect of about 50% improvement in gastric emptying, plateauing at a Cmaxfree level of about 30 ng/mL. See FIGS. 6A and 6B.

TABLE 4

Gastric Emptying in Healthy Volunteers Following a Single Dose on Day 1 and Following Multiple q8H Doses on Day 4 versus Pooled Placebo Subjects

| Gastric Emptying Day 1 Improvement Over Baseline | | Gastric Emptying Day 4 Improvement Over Baseline | |
|---|---|---|---|
| Ulimorelin | Placebo | Ulimorelin | Placebo |
| T25% @ 80 µg/kg | | T25% @ 80 µg/kg | |
| 30% | 2.8% | 35% | −28% |
| T50% @ 80 µg/kg | | T50% @ 80 µg/kg | |
| 14% | 3.5% | 26% | −9.3% |
| T25% @ 150 µg/kg | | T25% @ 150 µg/kg | |
| 45%* | 2.8% | 25% | −28% |
| T50% @ 150 µg/kg | | T50% @150 µg/kg | |
| 34%* | 3.5% | 23%* | −9.3% |
| T25% @300 µg/kg | | T25% @300 µg/kg | |
| 54%* | 2.8% | 31% | −28% |
| T50% @300 µg/kg | | T50% @300 µg/kg | |
| 46%* | 3.5% | 27%* | −9.3% |

*$p < .05$ for Paired t-test vs Baseline
t-test not performed at 80 µg/kg due to few number of subjects available With reference to Table 5, growth hormone levels in healthy volunteers spiked following administration of ulimorelin. Levels on Day 1 were meaningfully greater than those seen in placebo subjects at any timepoint (pooled placebo mean GH levels were 3.2 µg/L and ranged from about 0.1 to 11 µg/L). Over time, the spikes in GH levels diminished but remained measureable and within or slightly greater than the expected physiological range of the assay (0-0.8 µg/L for males and 0-8 µg/L for females).

TABLE 5

Peak Growth Hormone Levels in Healthy Male and Female
Volunteers Following Administration of Ulimorelin versus Placebo

| GH Dose (μg/kg) | Male Mean Max GH (μg/L) | | | Female Mean Max GH (μ/L) | | |
|---|---|---|---|---|---|---|
| | Day 1 | Day 4 | Day 7 | Day 1 | Day 4 | Day 7 |
| 0 | | 3.2 | | | 3.2 | |
| 150 | 11.4 | 2.4 | 1.7 | 18.8 | 10.7 | 6.2 |
| 300 | 18.7 | 4.0 | 3.0 | 41.5 | 31.5 | 11.3* |
| 600 | 41.7 | na | na | 77.9 | na | na |
| 900 | 79.7 | na | na | 83.4 | na | na |
| 1200 | 53.0 | na | na | 76.0 | na | na | na: Not applicable;
*n = 1.

Data from Tables 4 and 5 are from an as-yet incomplete Phase 1 study. An additional, fourth, healthy volunteer cohort is to be tested in an additional Phase 1 study and approval is presently being sought from regulatory authorities (Investigation Review Board or IRB) to dose that cohort at 600 μg/kg TID. In patients in the intent to treat population this dose is expected to be safe with regards to the potential impact of heart rate slowing on blood pressure, given typically elevated AAGP levels and a typically elevated sympathetic tone in such patients. However, for the fourth healthy volunteer cohort (i.e. the second Phase 1 study) it is possible that the IRB will deem this dose excessive for study, given normal AAGP levels and normal basal sympathetic tone. If so then a dose of 500 μg/kg TID will be tested in such healthy volunteers. Furthermore, even if approved by the IRB, the 600 μg/kg TID dose, in theory, could result in a Cmaxfree, particularly in an outlier subject, that is sufficiently high to cause not only a decrease in heart rate but also a decrease in blood pressure as would be documented by the presence of orthostatic hypotension. While this is highly unlikely and unexpected, should it occur to a degree that is deemed unacceptable during conduct of the study, the dose will be reduced from 600 μg/kg TID to 500 μg/kg TID.

A Phase 2a, multicenter, randomized, double-blind, comparator-controlled study of the efficacy, safety, and pharmacokinetics of multiple daily intravenous (IV) doses of ulimorelin (LP101) in patients with EFI can be conducted for the primary objective to evaluate the safety and tolerability of multiple daily IV doses of ulimorelin in patients with enteral feeding intolerance (EFI). Secondary objectives include: evaluate the pharmacodynamic (PD)-pharmacokinetic (PK) relationship following multiple daily IV doses of ulimorelin in patients with EFI and evaluate the effects of ulimorelin on gastric emptying and protein turnover (synthesis/degradation)

Patients would be randomized to ulimorelin (likely at two different doses, including for example a low dose of 300 μg/kg TID, and a high dose between 500 μg/kg and 600 μg/kg, TID) or (for the control arm) metoclopramide (10 mg) every 8 hours for 5-7 days, followed by, optionally, observation and assessments for an additional 24-48 hours. One or more of the following endpoints, or similar endpoints, can be measured, with assessment of the primary endpoint on Day 5 (or later if a longer study): daily average (mean) percentage of the target daily volume of enteral nutrition achieved, Days 1 through 5; Liquid gastric emptying (t1/2, 2 hour retention, 4 hour retention) in minutes on Day 4; Protein turnover (synthesis/degradation) on Day 4; Proportion of patients with feeding success, defined as the proportion of patients achieving 80% or greater of prescribed target rate of enteral nutrition, over Days 1 through 5; Days on mechanical ventilation; Days in the ICU; and/or % of patients experiencing pulmonary infections, which will be documented by predefined criteria.

Upon successful completion of such a Phase 2a study, i.e. if this study demonstrates, as expected, both safety and clinically meaningful effects on gastric emptying in the intent to treat population at the 600 μg/kg dose, a subsequent Phase 2b study may explore doses yet higher than these, for example 750 μg/kg or even higher if there is reason to believe that yet more clinical benefit may accrue. Conversely, Phase 2b and subsequent testing may continue at the same upper range as tested in the Phase 2a study.

Those of skill in the art, upon reading this disclosure, will appreciate that one can use the APACHE and nutritional risks scores, lean body mass, and biomarkers of response and enrichment strategies to identify patients eligible for enrollment in such a study whom might receive the greatest therapeutic benefit from ulimorelin administered in accordance with the invention due to their being at greatest risk from malnutrition and EFI.

Table 6 shows guiding information for such a clinical trial and the numbers of patients per treatment arm for demonstrating efficacy of ulimorelin to treat EFI as demonstrated by absolute increases in nutritional adequacy (NA), a proxy for increased calories delivered as a percentage of nutritional goals, at statistical significance and may be useful in designing a clinical trial powered to demonstrate that the methods of the invention are safe and efficacious in treating EFI in the ICU population and to provide the target increase in NA.

TABLE 6

Number of Patients per Treatment Arm to Achieve
Indicated Increases in Nutritional Adequacy (NA).

| | Number of Patients per arm | | |
|---|---|---|---|
| Absolute increase in NA | Assumes 30% feeding success in control arm | Assumes 50% feeding success in control arm | Largest n required for any control rate |
| 15% | 163 | 170 | 174 |
| 20% | 93 | 93 | 95 |
| 30% | 42 | 39 | 43 |
| 40% | 24 | 20 | 24 |

Assumptions: 80%, α = 0.05 (two-sided)
Feeding Success defined as reaching 80% of nutritional adequacy (caloric prescription)

In similar fashion, efficacious treatment of EFI as provided by the methods of the invention should result, over time, in improved patient outcomes, including, in some instances, decreased mortality rates and increase in ventilator-free days (VFD's) for those ICUs and other critical care centers adopting the present invention. Table 7 shows results consistent with a demonstration that the methods of the invention are efficacious in treating EFI, thereby decreasing mortality and increasing the number of VFD's in the ICU population. Specifically, as an example of potential beneficial outcomes in patients that treatment with ulimorelin in accordance with the invention may provide, the following table correlates absolute increase in percentage nutritional adequacy in the ICU with odds ratios, relative risk, and absolute value of decreases in 60-day mortality by percentage, as well as increases in Ventilator-Free Days (VFDs), as enabled by treatment of EFI with ulimorelin.

TABLE 7

Increase in nutritional adequacy vs. estimated effect

| Absolute increase in NA | OR of 60-day mortality | RR of 60-day mortality | Absolute decrease in mortality (%) | Increase in VFD (days) |
|---|---|---|---|---|
| 15% | 0.93 | 0.95 | 1.50% | 0.9 |
| 20% | 0.91 | 0.93 | 2.00% | 1.3 |
| 30% | 0.86 | 0.9 | 3.00% | 1.9 |
| 40% | 0.82 | 0.87 | 3.90% | 2.5 |

NA: nutritional adequacy (% caloric prescription received);
OR: odds ratio;
RR: relative risk;
VFD: ventilator-free days in first 60 days Ulimorelin dosed in accordance with the invention should have a marked beneficial impact on nutritional adequacy (the percentage of calories received over a period of time relative to the target caloric prescription over that same period of time, typically a day), and by providing such an effect, should therefore result in marked improvements in decreased mortality and increase in VFD.

Example 6—Treatment of EFI Patients

This example demonstrates, with illustrative patient examples, how a practicing physician may diagnose and treat patients in accordance with the invention.

Example 4 demonstrates that a physician may reasonably expect a significant number of EFI patients to be safely and efficaciously dosed by a single dose of ulimorelin despite AAGP variability. Furthermore, in many patients the initial dose administered results in especially pronounced gastric emptying effects. In other words, Cmaxfree from the first dose, even though lower than steady state Cmaxfree, produces a more profound improvement in gastric emptying than after several doses have been administered. In practice, therefore, the starting dose is expected to elicit a sufficient effect even if AAGP levels, once measured, warrant subsequent dose adjustment upwards. As such, the physician may choose to initiate therapy even without having first checked AAGP. In one such a case a physician treating an ICU patient with EFI may start dosing at 300 µg/kg, but more typically 600 µg/kg. In some cases the physician may proceed to continue dosing without checking AAGP at all, if satisfied with efficacy as indicated by resolution of EFI and with safety, where the assessment of the former will typically be done by noting an ability to provide enteral feeding successfully at a desired infusion rate (in mLs/hour or some functionally similar measure) without provoking a return of EFI (as measured by however the physician chooses to measure, but potentially including GRV, abdominal distension or any of other methods cited elsewhere herein), and, the assessment of the latter by the absence of an undesirable slowing of heart rate for which there is no other obvious cause other than being a ulimorelin side effect.

If the physician is unsatisfied with efficacy, has concerns about safety, or, for other reasons related to patient clinical course, such as described below, elects to measure AAGP, he or she may, in some cases, do so at any time during treatment. In other embodiments, the physician may have already checked AAGP roughly contemporaneously with (or shortly before or after) initiation of therapy, particularly if the patient has heart disease that predicts a higher than normal potential for suffering ill effects of a mild slowing of heart rate, thus suggesting that the patient will have less tolerance for an otherwise tolerated Cmaxfree. In one embodiment, the purpose of the testing, or re-testing, is for the physician to gain comfort that the AAGP is in such a range as to ensure that doses administered are achieving desired, and not excessive, Cmaxfree. In some embodiments, the purpose is to confirm that the AAGP is in a range known by the physician to ensure that dose adjustment, either upwards or downwards, is not advised. No matter when AAGP is checked, if the result is an AAGP below normal, the physician may choose to lower the dose, by way of non-limiting examples, to a dose in the range 150 µg/kg to 300 µg/kg from the starting dose of, e.g., 600 µg/kg. If the result is an AAGP particularly above normal, such as 250 or 300 mg/dL—said cases equating to Multiple Ratios as used herein of 5 or 6—the physician may elect to increase the dose of ulimorelin, such as, by way of non-limiting example, from 600 µg/kg to high doses including up about 1200 µg/kg TID. That said, as most patients will have AAGP levels in the 50-250 range, corresponding to Multiple Ratios of 1-5, the physician may readily expect no such adjustment to be necessary when using a starting dose of 600 µg/kg, particularly when treating primarily for gastric emptying effect as opposed to dosing to achieve a significant reduction in net sympathetic tone.

It will be appreciated that in the alternative, the physician could similarly measure the patient's ulimorelin Cmaxfree to ensure it is above a minimally needed amount for efficacy and below a maximal amount for safety, and that this measurement has the advantage of being more intuitive, as physicians are accustomed to measuring levels of prescribed drugs achieved in their patients' bloods. Checking AAGP, rather than Cmaxfree, has an advantage, among others, of lacking the requirement of having to time a blood sample collection around the timing of a specific drug infusion event (i.e. in order to capture the resultant Cmaxfree) since AAGP levels, whether low, normal or elevated, do not typically change as acutely as ulimorelin Cmaxfree does, and since once elevated, AAGP tends to stay elevated for at least several hours to as long as days, unlike Cmaxfree which is a highly transient event.

While the frequency of re-testing AAGP, or decision to test it in the first place, is ultimately at the physician's preference, certain clinical events and findings, upon their occurrence, may suggest a value to test or re-test—in particular, events that often correlate with changes in AAGP level, whether increase or decrease. One such event is a surgical procedure. Another is a new significant infection or a significant worsening of a known infection, such as, without limitation, the development of pneumonia or sepsis. Exacerbation, or de novo development of a medical condition with a significant inflammatory component, is another such example. In some embodiments, these same medical conditions may guide the physician to choosing a particular starting dose, and in one embodiment, to choose a higher starting dose such as, by way of nonlimiting example, 750 µg/kg rather than 600 µg/kg. Long duration of pre-existing illness prior to transfer to an ICU is a potential reason to initiate dosing at a higher rather than lower dose, as the expectation is that AAGP will be elevated; indeed, the physician may elect to confirm this by checking AAGP before, concurrent with, or shortly after initiating therapy. As such and in another embodiment, when treating a patient who has any of the clinical course described herein, or other reasons making a physician suspect an elevated AAGP, the physician may also elect to initiate dosing at, or change dosing to, for example, 750 µg/kg given the expectation of a higher AAGP, whether or not s/he actually checks AAGP at the time of dose initiation.

Another reason to re-test an earlier AAGP is simply that the initial test was abnormal. Conversely, if the initial AAGP was between 40-60, i.e. in the normal range, or up to 100, i.e. a Multiple Ratio of 2 or less, then the physician, especially absent intercurrent medical developments such as those listed above, may elect not to re-test AAGP, or to do so less frequently. The frequency of retest, if at all, may typically be daily, once every 2-4 days, up to as long as once per week or less frequent. A specific reason to re-test will typically result in more frequency of testing.

Furthermore, and whether or not AAGP is tested, the present invention offers the physician a way to follow the patient's clinical course to assess whether a prescribed dose is sufficient, too high or too low. Regardless of the initial dose or the dose being given at the time, if said dose is higher than optimal, i.e. resulting in a Cmaxfree that is too high, then patients will have an increased propensity to manifest a mild slowing of heart rate shortly after completion of dose administration (i.e. at or near the time of achieving Cmaxfree). Such slowing, if not desired, may guide the physician to decrease the subsequent dose, e.g. and by way of non-limiting examples, from 600 µg/kg to 300, 300 µg/kg to 150 µg/kg, etc. Awareness of this phenomenon may guide the physician and supporting ICU staff to pay attention to a patient's heart rate (HR) using standard clinical practices to do so around the time of completion of infusion. Evidence of undesireable HR slowing will further suggest that checking AAGP may be advised as the AAGP may be lower than expected (either de novo or due to having fallen towards or below normal after having been previously elevated). In a related embodiment in which a patient's clinical course may be used to assess for optimal dosing, to assess efficacy with or without checking AAGP (or Cmaxfree) the physician may simply follow clinical course for desired resolution of EFI.

In a patient for whom the treating physician suspects, or has evidence of, a level of sympathetic tone that is unhealthy, excessive and/or otherwise may be deemed deleterious to the patient, the physician may elect to derive benefit from ulimorelin's propensity, at high enough doses, to cause an mild decrease of heart rate and to continue dosing, or indeed to aim to dose from the outset, at levels that will cause such decrease. Excess levels of sympathetic tone are common in critically ill patients. While not wishing to be bound by theory, ulimorelin's effects to slow the heart rate, are exerted, at least in part, via increased vagal (parasympathetic) activity (tone) and/or decreased sympathetic tone, i.e. tilting the balance of parasympathetic vs. sympathetic tone in favor of more parasympathetic (and thus less sympathetic). The more parasympathetic tone, the lower the heart rate. Likewise, the more heart rate slowing, the more parasympathetic tone, due to treatment with ulimorelin. It is known that decreasing heart rate using beta blockers may both be done safely in many critically ill patients and that doing so offers as benefits: exerting a cardioprotective effect, attenuating catabolic response, and reversing the elevation of resting energy expenditure. All of these may prove beneficial to the ICU clinical course and/or longer-term outcomes of critically ill patients. The increased vagal activity of ulimorelin is functionally the same as the activity of beta blockers with specific regard to the balance of parasympathetic vs. sympathetic tone. As such, i.e., given the benefits of beta blockade, a physician may not only choose to ignore minor decreases in heart rates in their critically ill patients receiving ulimorelin treatment but may even choose to seek to achieve such decreases both for cardioprotection and/or as a sign that the drug is providing the additional benefits of increased parasympathetic tone. In such cases the physician may continue to treat without changing ulimorelin dose, i.e. despite a documented mild heart rate slowing. Similarly, the physician may choose not to check an AAGP level, since s/he will have no intent to change the dose and as such does not need to know the AAGP level, unless, of course, the physician has another reason to want to adjust dose such as, for example, dissatisfaction with the drug's effect on gastric emptying.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method of treating a patient receiving enteral feeding in an intensive care unit (ICU) and exhibiting enteral feeding intolerance (EFI), comprising administering ulimorelin to the patient by intravenous infusion three times daily at approximately 8 hour intervals (q8H), wherein ulimorelin is administered at a dose of 600 µg/kg patient body weight per infusion.

2. The method of claim 1, wherein the patient is receiving enteral feeding via a nasogastric tube.

3. The method of claim 1, wherein ulimorelin is administered by a 30 minute intravenous infusion.

4. The method of claim 1, wherein the patient's plasma alpha 1-acid glycoprotein (AAGP) level is not determined at the time the treatment is initiated.

5. The method of claim 4, wherein the patient's AAGP level is not measured during the course of the treatment.

6. The method of claim 5, wherein ulimorelin is administered to the patient for at least 3 days.

7. The method of claim 6, wherein ulimorelin is administered for no more than seven days.

8. The method of claim 1, wherein ulimorelin is administered to the patient for at least 3 days.

9. The method of claim 8, wherein ulimorelin is administered for no more than seven days.

10. The method of claim 8, wherein the patient receiving ulimorelin has a plasma alpha 1-acid glycoprotein (AAGP) level that is elevated relative to the plasma AAGP level of a healthy individual.

11. The method of claim 1, wherein the patient receiving ulimorelin has a plasma alpha 1-acid glycoprotein (AAGP) level that is elevated relative to the plasma AAGP level of a healthy individual.

12. The method of claim 1, wherein the dose is not guided by measurement of alpha 1-acid glycoprotein (AAGP) levels and provides a common dosage for a population of patients in an intensive care unit (ICU) exhibiting enteral feeding intolerance (EFI).

13. A method of treating a population of critically ill patients admitted to an intensive care unit (ICU), wherein the patients require enteral feeding, the method comprising administering ulimorelin by intravenous infusion three times daily at approximately 8 hour intervals (q8H), wherein ulimorelin is administered at a dose of 600 µg/kg patient body weight per infusion.

14. The method of claim 13, wherein the patients' plasma alpha 1-acid glycoprotein (AAGP) level is not determined at the time the treatment is initiated.

15. The method claim 13, wherein the critically ill patients are patients with a condition selected from the group consisting of a condition requiring mechanical ventilation, trauma, sepsis, cardiopulmonary disease, neoplasm, pneumonia, surgery, and gastrointestinal disease.

* * * * *